US012734275B2

(12) United States Patent
Olivos Meza et al.

(10) Patent No.: US 12,734,275 B2
(45) Date of Patent: Sep. 15, 2026

(54) ALLOGENEIC IMPLANTS FOR THE TREATMENT OF CARTILAGE INJURIES

(71) Applicant: Anell Olivos Meza, Veracruz (MX)

(72) Inventors: Anell Olivos Meza, Estado de México (MX); Carlos Landa Solís, Estado de México (MX); Carlos Enrique Suarez Ahedo, Tlalpan (MX); Maria Luisa Siliceo Rodriguez, Veracruz (MX); Clemente Ibarra Ponce De Leon, Veracruz (MX)

(73) Assignee: Anell Olivos Meza, Veracruz (MX)

( * ) Notice: Subject to any disclaimer, the term of this patent is extended or adjusted under 35 U.S.C. 154(b) by 0 days.

(21) Appl. No.: 17/223,377

(22) Filed: Apr. 6, 2021

(65) Prior Publication Data

US 2022/0313869 A1 Oct. 6, 2022

(51) Int. Cl.

| | |
|---|---|
| ***A61L 27/38*** | (2006.01) |
| ***A61L 27/36*** | (2006.01) |
| ***C12N 5/077*** | (2010.01) |
| *A61F 2/30* | (2006.01) |

(52) U.S. Cl.

CPC ....... *A61L 27/3817* (2013.01); *A61L 27/3633* (2013.01); *A61L 27/3654* (2013.01); *A61L 27/3683* (2013.01); *C12N 5/0655* (2013.01); *A61F 2/30756* (2013.01); *A61L 2430/06* (2013.01)

(58) Field of Classification Search

CPC combination set(s) only.
See application file for complete search history.

(56) References Cited

U.S. PATENT DOCUMENTS

| | | | | |
|---|---|---|---|---|
| 8,518,433 B2 * | 8/2013 | Kizer | ...................... | A61P 19/04 424/426 |
| 2014/0134212 A1 * | 5/2014 | Shi | ...................... | A61L 27/3683 424/548 |
| 2020/0208113 A1 * | 7/2020 | Jenner | .................. | A61L 27/225 |

FOREIGN PATENT DOCUMENTS

| | | |
|---|---|---|
| EP | 2338441 | 6/2011 |
| EP | 2919794 | 9/2015 |
| WO | WO2019113558 | 6/2019 |

OTHER PUBLICATIONS

Roseti et al. (2011) Development of Human Chondrocyte-Based Medicinal Products for Autologous Cell Therapy. Biomaterials Science and Engineering. InTech. DOI: 10.5772/24954 (Year: 2011).*
Wolf et al., European Cells and Materials vol. 15 2008 (pp. 1-10). (Year: 2010).*
Kim et al., Knee Surg Sports Traumatol Arthrosc (2010) 18:528-534. (Year: 2010).*
Adkisson IV et al., Am J Sports Med. Jul. 2010; 38(7): 1324-1333 (Year: 2010).*
Munirah et al., European Cells and Materials vol. 15, 2008 (pp. 41-52). (Year: 2008).*
Abazari et al., Cryobiology 66 (2013) 201-209. (Year: 2013).*

* cited by examiner

*Primary Examiner* — Robert S Cabral
(74) *Attorney, Agent, or Firm* — Defillo & Associates, Inc; Evelyn A. Defillo

(57) ABSTRACT

A graft or construct including an isolated cartilage chondrocytes from young donors (<20 years), seeded on a three-dimensional membrane composed of one of the main chondrogenesis-promoting substances (hyaluronic acid), in high densities (1×106) with autologous serum and sealed with a fibrin adhesive for the treatment of a cartilage lesion, with tissue formation that has greater durability, at a lower cost and with fewer risks than the treatments currently available for the management of such lesions. Likewise, a procedure for the treatment of articular cartilage lesions is provided, through the implantation of allogeneic chondrocyte grafts that present the capacity to generate or repair satisfactorily the cartilage of the lesion.

3 Claims, 13 Drawing Sheets

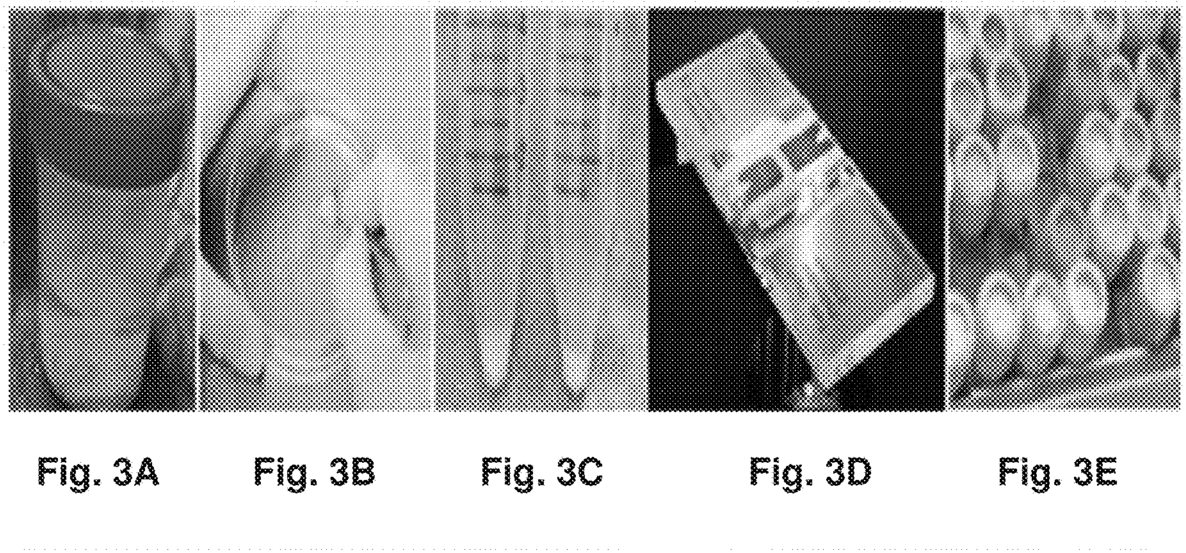
Fig. 3A Fig. 3B Fig. 3C Fig. 3D Fig. 3E
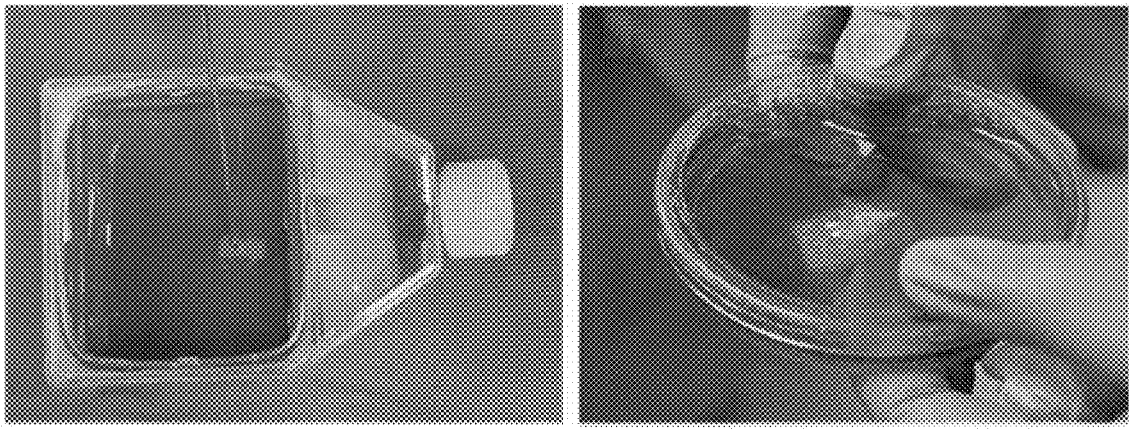
Fig. 4A Fig. 4B
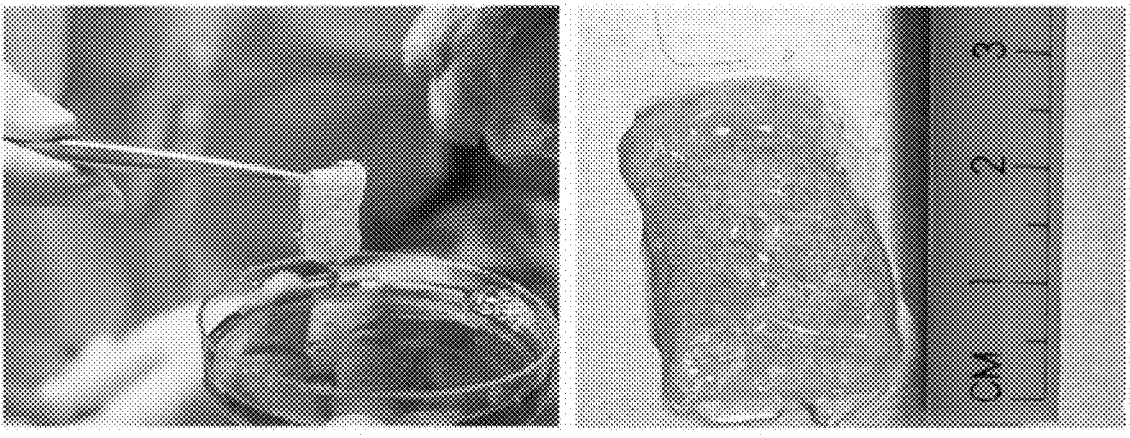
Fig. 4C Fig. 4D

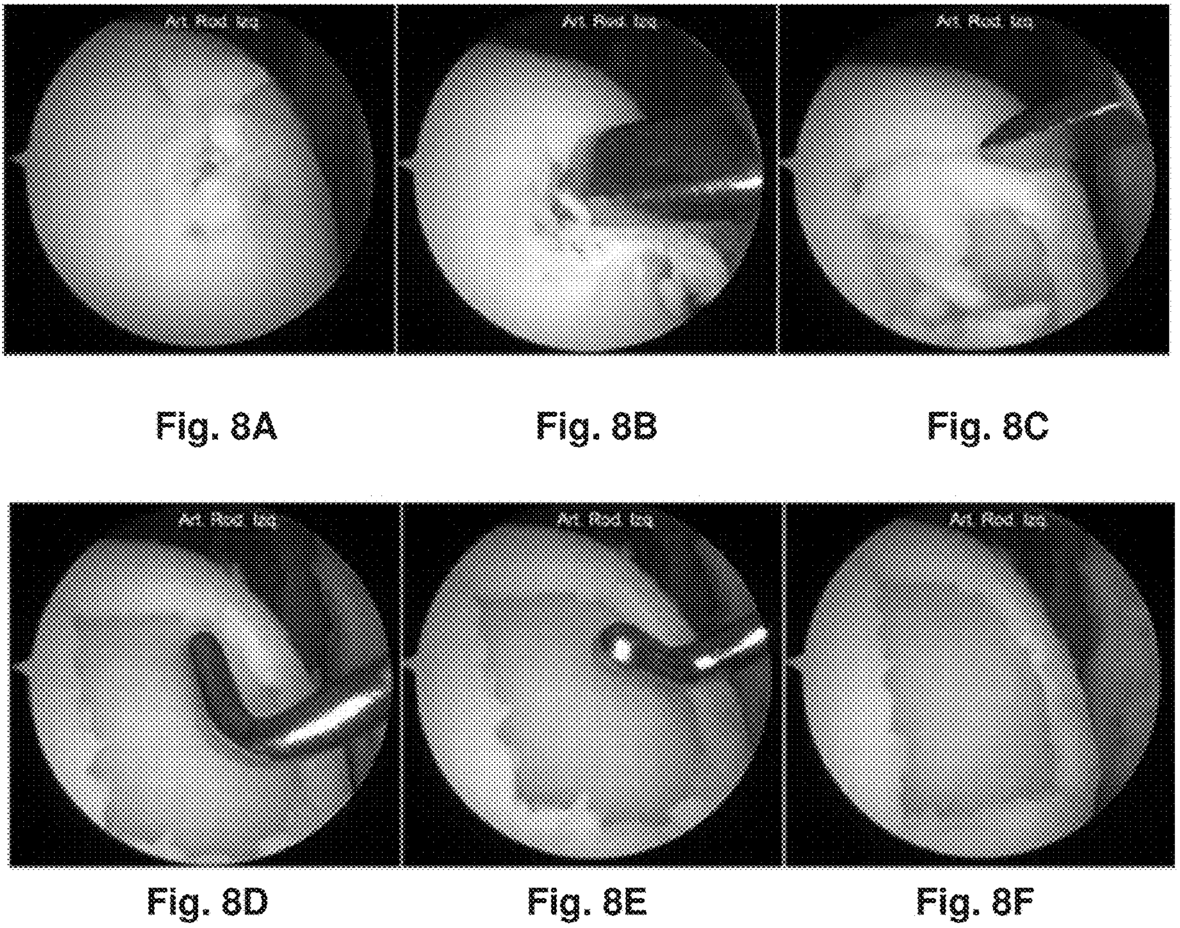
Fig. 8A Fig. 8B Fig. 8C
Fig. 8D Fig. 8E Fig. 8F
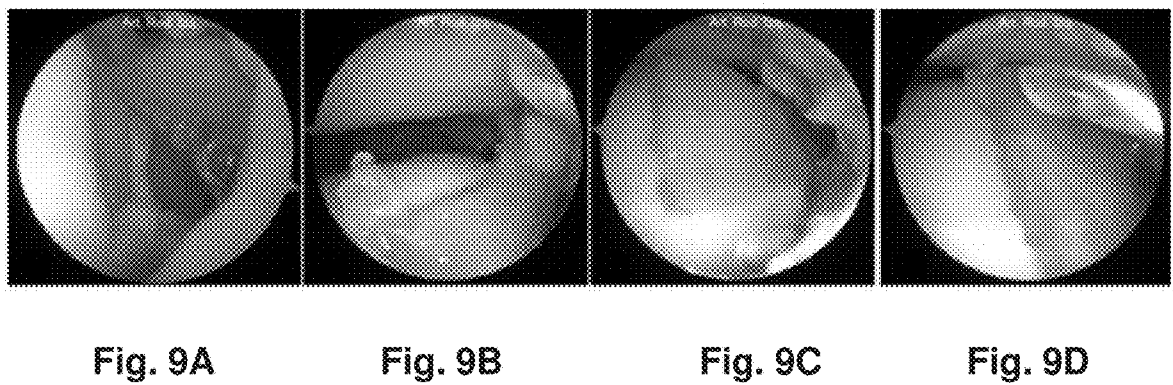
Fig. 9A Fig. 9B Fig. 9C Fig. 9D

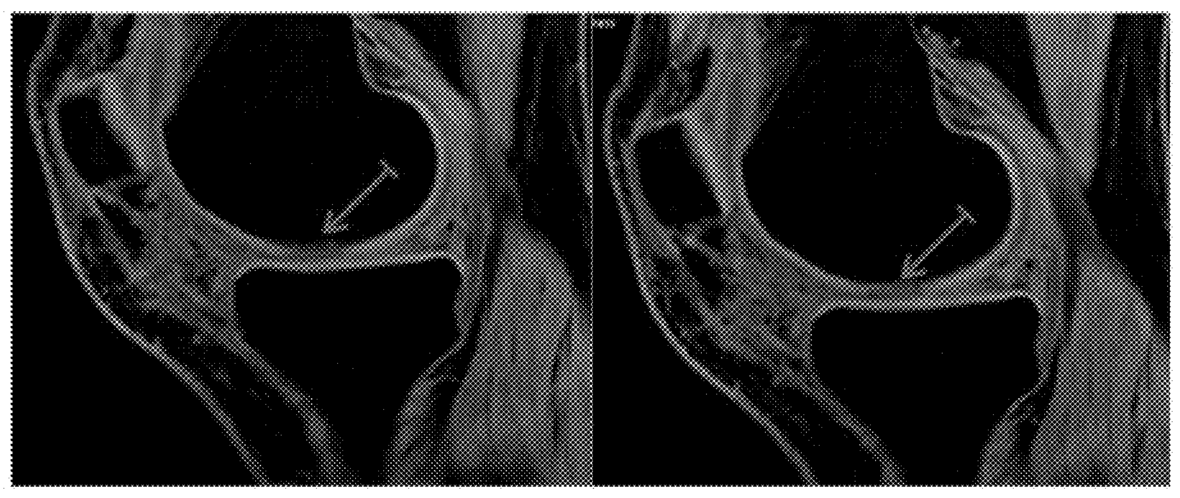
Fig. 10A
Fig. 10B
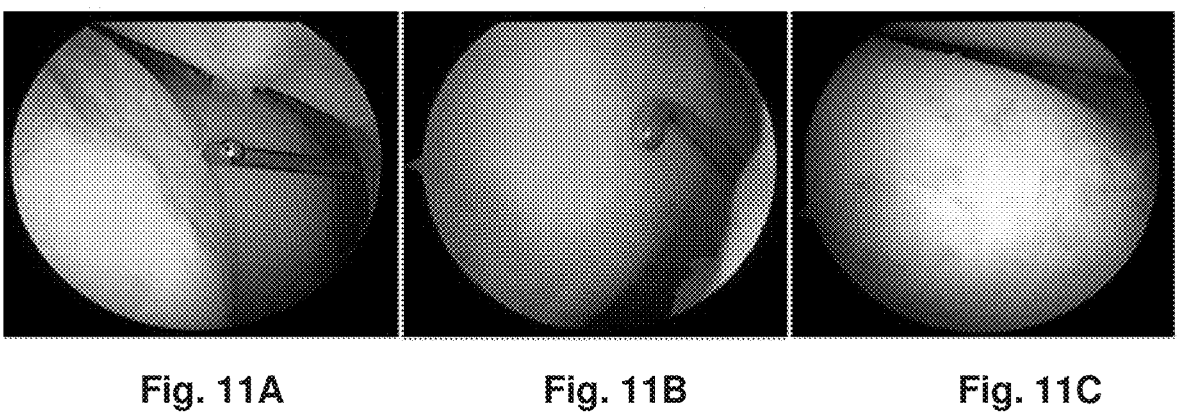
Fig. 11A
Fig. 11B
Fig. 11C
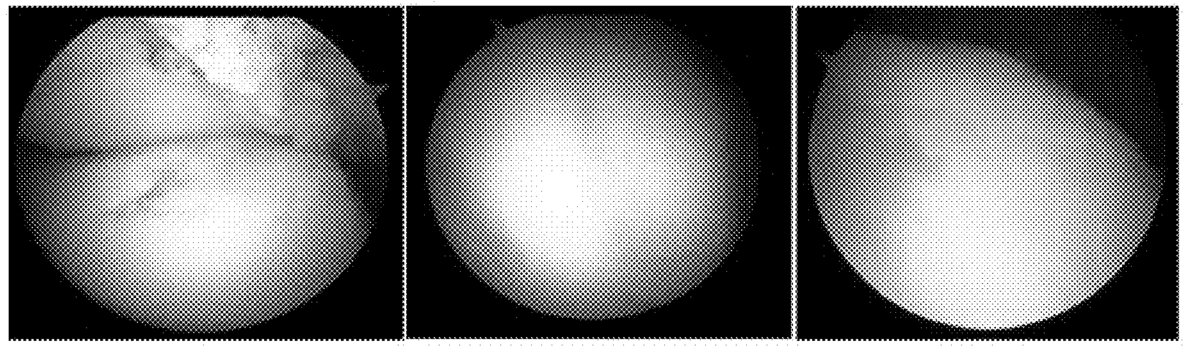
Fig. 11D
Fig. 11E
Fig. 11F

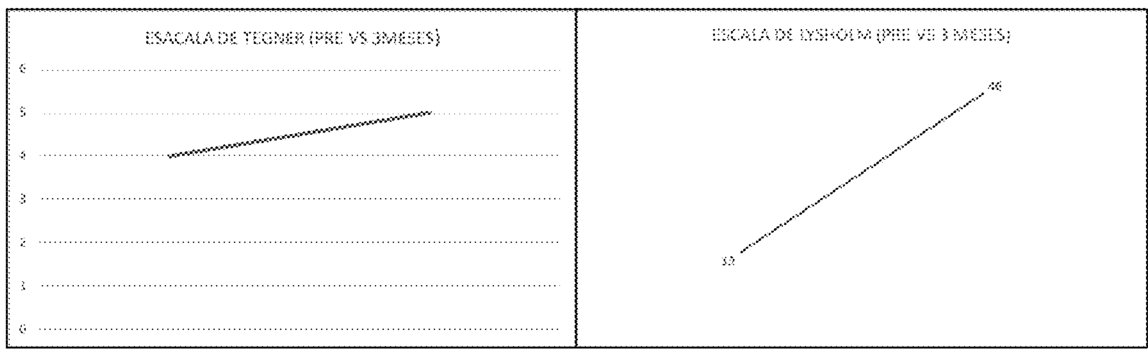
Fig. 18A
Fig. 18B
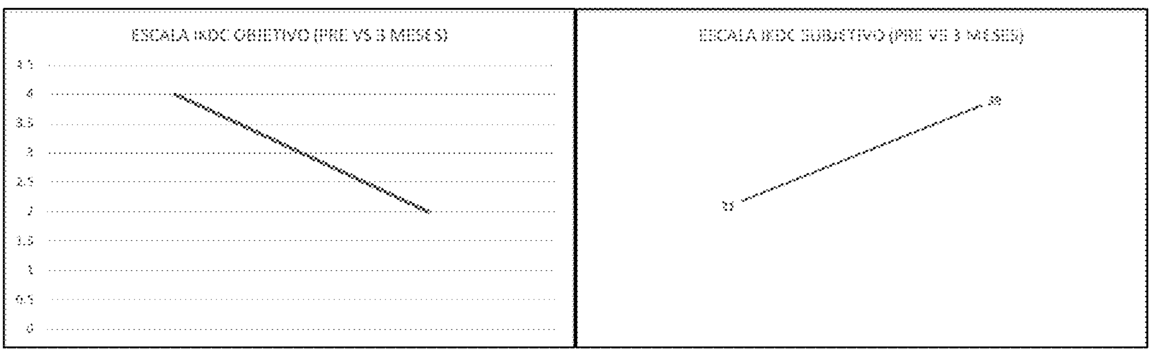
Fig. 18C
Fig. 18D
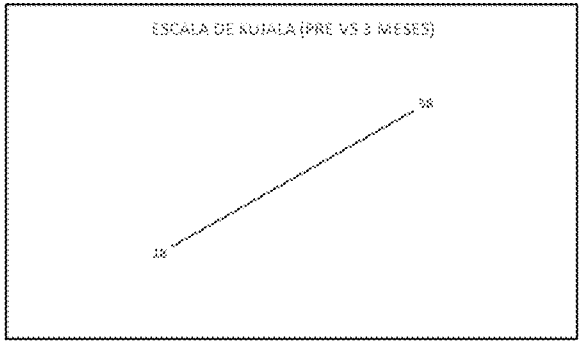
Fig. 18E

ALLOGENEIC IMPLANTS FOR THE TREATMENT OF CARTILAGE INJURIES

TECHNICAL FIELD OF THE INVENTION

The present invention is located in the field of medicine, particularly in cell therapy and tissue engineering, refers to methods of treatment of articular cartilage lesions, in particular knee cartilage lesions. It also refers to the development of an implant or construct of allogeneic chondrocytes for the treatment of these cartilage lesions.

BACKGROUND OF THE INVENTION

Cartilage injuries in weight-bearing joints such as the knee, ankle and hip are difficult to heal without surgical treatment. The incidence of this type of injury is high in young patients (30-35 years), especially in the knee joint, being found in up to 65% of the arthroscopies performed in this joint to treat other pathologies (ligament and/or meniscus injuries). 1-4 The consequences of not treating these injuries adequately and timely are pain, gradual loss of function, disability and early osteoarthritis. 3,4 Evidently this type of injury is a major health problem with an important epidemiological repercussion and a great impact on health and quality of life that generates significant costs for individuals, institutions and the health system in general.

Currently there are several surgical techniques to treat cartilage lesions with varying results. However, in spite of such diversity of techniques, they present inconveniences that need to be overcome for the good of the patient, his quality of life, treatment and recovery times and, of course, economic costs. Autologous Chondrocyte Implantation (ACI) has been documented as the treatment that has provided the best long-term results in terms of pain relief, improved function and delay in the development of early osteoarthritis4,5. ACI is currently the only cell therapy for cartilage repair in the UK.

This technique was performed and published by two Swedish orthopedists in 1987, until 2010 had been performed 35,000 cases worldwide, reporting that up to 87% of patients undergoing this procedure have clinical results that are classified as good to excellent, compared to other techniques (microfractures, autologous osteochondral transfer, augmented microfractures) that show fewer encouraging results.

The ACI technique is a two-stage surgical procedure. In the first surgical procedure, cartilage biopsies are taken from a “no load” area of the patient’s own knee (autologous). The cartilage biopsy is sent to the laboratory, where the cartilage-producing cells (chondrocytes) are extracted and cultured in vitro for a period of 6 to 8 weeks in order to increase the number of available cells, which will be used in the following surgical procedure. Once the appropriate amount of cells is available, a second arthroscopy is performed to place the chondrocytes in the lesion, previously cultured on a commercially available polymer of hyaluronic acid, to promote the formation of a tissue very similar to cartilage over time, repairing the defect, relieving the symptoms of the injury; this allows the patient to resume daily life activities, and even, in the long term, to perform sports activities.

Over time, the ICA technique has undergone multiple modifications, which are usually referred to as “generations”. Currently, 3 generations are recognized, with the goal of counteracting complications and improving long-term results. In the 3rd generation, an important modification is that the autologous chondrocytes are seeded in a collagen matrix to be subsequently placed in the defect or site of injury, this reduces the runoff and loss of chondral cells out of the matrix as happened in the 1st and 2nd generation. The third generation is also known as MACI (Matrix Associated Chondrocyte Implantation), and has shown better results than previous generations. It has been observed that culturing the cells on the matrix is more effective than injecting them into the defect and then covering it with a membrane sutured to the adjacent cartilage. Although the results with this MACI technique are better than those obtained with previous generations, this technique still has several drawbacks, among which are the high costs of the same and even more limiting is the inability of any hospital or health institute can put it into practice by the infrastructure required and trained personnel to perform the work of tissue engineering.

The high economic cost of this treatment is due to the fact that two surgical procedures are required, in addition to the large amount of time required for cell culture, including laboratory material, infrastructure and human resources; which amounts to 17,000 Euros in European countries6 and approximately $250,000 in Mexico.

Another major limitation is also presented in the source of autologous cartilage, since this requires taking healthy cartilage from a knee of the same patient, which implies 2 problematic scenarios for the patient, on the one hand, there is the limitation of the amount of healthy cartilage that can be taken from the patient and, on the other hand, it generates a great risk of developing premature joint wear in the donor area (early osteoarthritis).

In order to reduce costs and the two-step procedure, a one-step technique called STACI (Single treatment Autologous Chondrocyte Implantation) has been described in which the laboratory is taken to the operating room and during the surgery to take a cartilage biopsy, the chondrocytes are isolated with an enzymatic procedure, expanded stimulated with growth factors in one hour and mixed with mononuclear bone marrow cells, obtained from the same patient. This mixture of cells is seeded onto a matrix of collagen or hyaluronic acid, to be placed in the lesion during the same procedure. The two-year results of STACI (one surgery) are similar to those reported for ACI (two surgeries), however, the reduced costs make this technique an attractive option for cartilage regeneration. 7

Allogeneic chondrocyte implantation has currently been explored to address the limitations and multi-step technique required for autologous chondrocyte implantation, however, the literature is still limited. 8

In the patent literature we found document EP2919794, which refers to compositions for use in methods of treatment of a cartilage, bone, ligament, tendon, meniscus, joint or muscle defect in a subject. In one embodiment, the method comprises administering a composition of fragmented or particulate cartilage (0.25 to 5 mm), derived from cadaveric human donor, wherein said cartilage particles possess viable chondrocytes and further contains a biocompatible vehicle, comprising a cryopreservation solution (DMSO+serum) or culture medium (DMEM+5% SFB; DMEM high glucose).

Patent document EP2338441 refers to a product also composed of cartilage fragments or particles derived from cadaveric donor, but in this case from young donors (under 15 years of age), which enhances a greater capacity to form hyaline cartilage matrix compared to that which can be produced with chondrocytes from adult donors. The product is presented as a kit in a sterile container for the treatment of cartilage lesions composed of fragmented cartilage particles from cadaveric donor containing viable chondrocytes and a storage solution.

A major disadvantage of the previously described patents is that cadaveric donor-derived cartilage retains the extracellular matrix, although it functions as a three-dimensional scaffold, as a chondroreactor for the fragmented cartilage particles, it is also true that this matrix also represents a greater risk of immune response and rejection reactions by the recipient, since the cartilage contains donor proteins that can be identified by the recipient and produce from a simple rejection mechanism, which prevents the formation of the desired tissue and its integration, to a major immunological reaction both locally and systemically.

A further disadvantage of the technology described in said patents arises from the fact that the tissue is derived from rib cartilage, nasal cartilage, tracheal cartilage, sternal cartilage and other unspecified sources of cartilage, the nature, composition and structure of which is very different from that of joint cartilage (knee, ankle, hip, shoulder), whereby it is desirable that the chondrocytes are derived from hyaline cartilage, mainly from knee (as in the case of the present invention) to form articular cartilage.

Patent document WO 2019/113558 A1 discloses the treatment of chondral and osteochondral lesions, using a composition of allogeneic cells, cryopreserved in a cell bank, cultured on a porcine collagen resorbable membrane (type I and/or II), at a density of 250,000 cells per cm2. This document indicates that chondrocytes can be obtained from "various tissues", which implies the possibility that the cells obtained are not chondrocytes specific for hyaline cartilage. On the other hand, before cryopreservation of the chondrocytes, they are expanded and cultured for at least two passages (in one section they describe less than 5), which conditions a dedifferentiation of the primary chondrocytes and therefore a high risk of fibrocartilage formation instead of hyaline cartilage. In addition, another event that may condition the formation of fibrocartilage instead of hyaline cartilage is the low density of cells that are seeded in the collagen membrane, another factor that favors cellular dedifferentiation and the formation of fibrous tissue.

On the other hand, there is also the disadvantage that the chondrocyte cultures are supplemented with fetal bovine serum, a serum of animal origin that can clearly trigger immunogenic reactions in a human recipient.

Purpose of the Invention

The present invention refers to an orthopedic implant formed by cadaveric allogeneic chondrocytes on a support or membrane of hyaluronic acid, sealed with a fibrin adhesive, for the treatment of a cartilage lesion, with tissue formation that has a greater durability, at a lower cost and with fewer risks than the treatments currently available for the management of such lesions.

Another object of the present invention refers to a kit for the treatment of cartilage comprising an orthopedic implant, conformed by allogeneic chondrocytes, derived from cadaveric donor, seeded on a hyaluronic acid membrane and covered are a biocompatible adhesive, wherein said chondrocytes are adhered to the membrane and present the formation of extracellular matrix; wherein said container further comprises a culture medium, supplemented with autologous serum and antibiotic-antimycotics.

Another object of the present invention refers to a procedure for the treatment of articular cartilage lesions, by means of the implantation of an orthopedic construct formed by cadaveric allogeneic chondrocytes on a support or membrane of hyaluronic acid, sealed with a fibrin adhesive, where said chondrocytes are adhered to the membrane and present the formation of extracellular matrix.

BRIEF DESCRIPTION OF FIGURES

FIGS. 2A-2D show once a tissue donor is identified, both knees are arthrotomized and cartilage fragments are taken.

FIGS. 2E-2F show the tissue donor of FIG. 2D placed in sterile containers containing physiological solution or culture medium (DMEM-F12) supplemented with 10% antibiotic-antimycotic. At the biopsy procurement site, donor data are documented to standardize characteristics that may influence the viability and chondrogenic capacity of the cells (age, gender, associated pathologies and cause of death). Likewise, associated variables such as time of death and time between death and cartilage harvesting are also verified.

FIGS. 3A-3E show an isolation method and viability determination of chondrocytes derived from cadaveric donor cartilage. Briefly, the tissue is washed several times with PBS and 10% antibiotic-antimycotic, until fluids and donor debris are completely removed (3A). Subsequently, a mechanical digestion is performed with a scalpel, to obtain tissue fragments smaller than 1 mm (3B), followed by an enzymatic digestion in which collagenase-type 2 (0.1 to 0.3% w/v) is used, for at least 1 hour at 37° C., under continuous agitation, the supernatant containing the cells released by the previously described digestions is recovered (3C), and the undigested fragments are subjected to a second stage of digestion with a fresh enzymatic solution, for at least another hour at 37° C.

Cell number and viability are determined by counting in Neubauer chamber and trypan blue (3D). Isolated chondrocytes are cryopreserved (3E) without expanding, in order to preserve and maintain both the viability, morphology and functionality of the same, various methodologies are known in the state of the art for this purpose. The freezing medium comprises culture medium, commercial human serum or autologous serum and a cryoprotective substance. In one embodiment of the present invention, the chondrocytes obtained were deposited in freezing medium [DMEM/F12 (80%), autologous serum (10%) and DMSO (10%)], at a density of a maximum of 500,000 cells per ml of medium, and cryopreserved in liquid nitrogen or at −80-192° C.

FIGS. 4A-4D show a Graft Kit or three-dimensional construct. The figures show a kit for the treatment of cartilage comprising an orthopedic implant, formed by allogeneic chondrocytes, derived from cadaveric donor, seeded on a hyaluronic acid membrane and covered with a biocompatible adhesive, where said chondrocytes are adhered to the membrane and present the formation of extracellular matrix;

where said container also comprises a culture medium, supplemented with autologous serum and antibiotic-antimycotics.

FIGS. 5A-5D show the presence of proteoglycans in the formed cartilage. Histological sections of tissue formed from allogeneic cadaveric chondrocytes of the present invention (5B), chondrocytes derived from living donor (P0), without expansion or cryopreservation (5C), chondrocytes derived from living donor (P2) expanded for 2 passes, without cryopreservation (5D) and hyaline cartilage control tissue (5A), stained with alcian blue that allows identification of the characteristic extracellular matrix of hyaline cartilage.

FIGS. 6A-6D show quantitative evaluation of the quality of the formed cartilage. Quantitative analysis of histological staining was carried out by three independent and blinded observers using the modified O'Driscoll histological scale. This assesses the amount of cartilage formed, as seen by red staining, scoring 80-100% (8 points), 60-80% (6 points), 40-60% (4 points), 20-40% (2 points) and 0-20% (0 points); integrity of the formed tissue structure, scoring as follows: Normal (2), mild disruption (1) and severe lack of integration (0); Cellularity, which assesses how similar the shape of the cells is to normal cartilage and how many cells there are, scoring as follows: normal cellularity (3), hypocellularity<25% (2), moderate hypocellularity>25% (1), severe hypocellularity (0).

At least three fields of each histological slice were evaluated. A maximum score of 14 was given to the native cartilage (FIG. 6A); the closer the score is to 14, which is assigned to the histological specimens, the higher the quality of the formed tissue and the closer it is to healthy cartilage.

Figure 7:
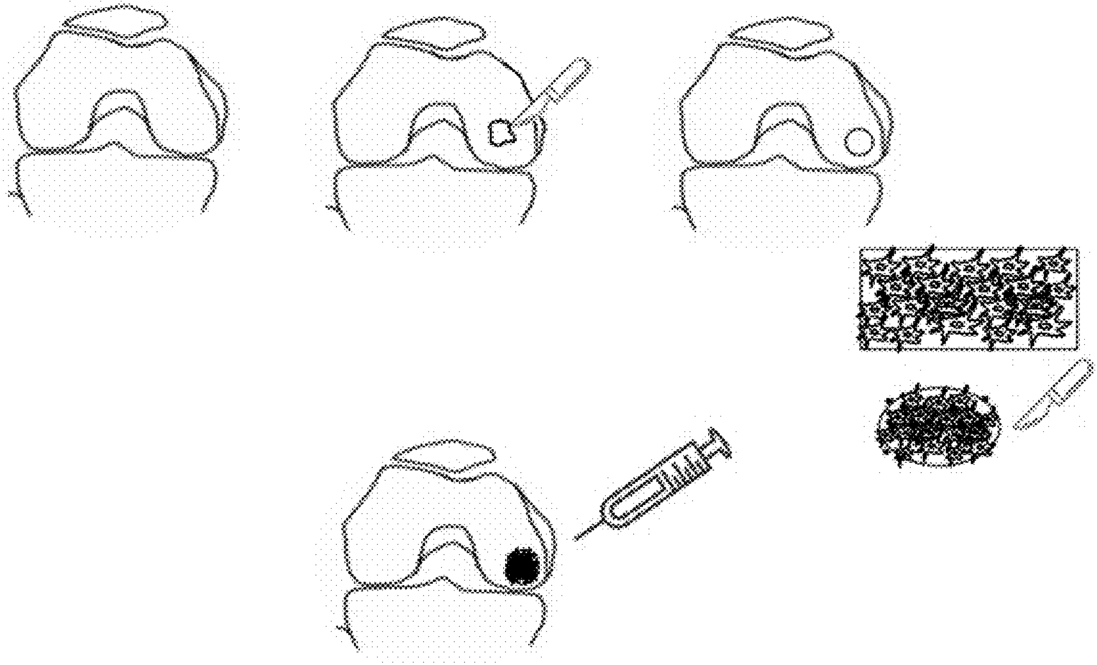

FIG. 7 shows a schematic diagram of the procedure for placing the implant or construct in the lesion area.

FIGS. 8A-8F show a preparation and measurement of lesion size by arthroscopy. The figures show an image of the lesion to be treated (8A), and the debridement of the edges of the lesion (8B, C8), to obtain a square or rectangular shaped area (8F) and the measurement in height and width using an arthroscopic hook probe (8D and 8E).

FIGS. 9A-9D show an implantation and fixation of the construct at the site of injury. The Figures show how the implant or construct is introduced to the lesion area (9A), as well as its extension on the surface of the lesion (9B), ensuring the contact of the graft with all the edges of the adjacent native cartilage (9C) and the coating with the fibrin adhesive (9D).

FIGS. 10A-10B show an evaluation process of construct integration by NMR. A Nuclear Magnetic Resonance Imaging study of a knee treated with the implant of the present invention is shown showing the tissue generated at 12 months with adequate contact to the native cartilage.

FIGS. 11A-11F show a 12-month cartilage lesion repair: ACI vs ALCI Arthroscopic evaluation, 12 months after treatment of cartilage lesion in the lateral trochlea of both knees in the same patient. In Figures A through C, we show images of the right knee, with lesion of 20×15 mm, was treated with autologous chondrocyte implantation (ACI); On the other hand, the left knee (FIGS. 11D, 11E and 11F), with 18×15 mm lesion, was treated with the allogeneic chondrocyte implantation of the present invention (ALCI).

Figures 12A, 12B:
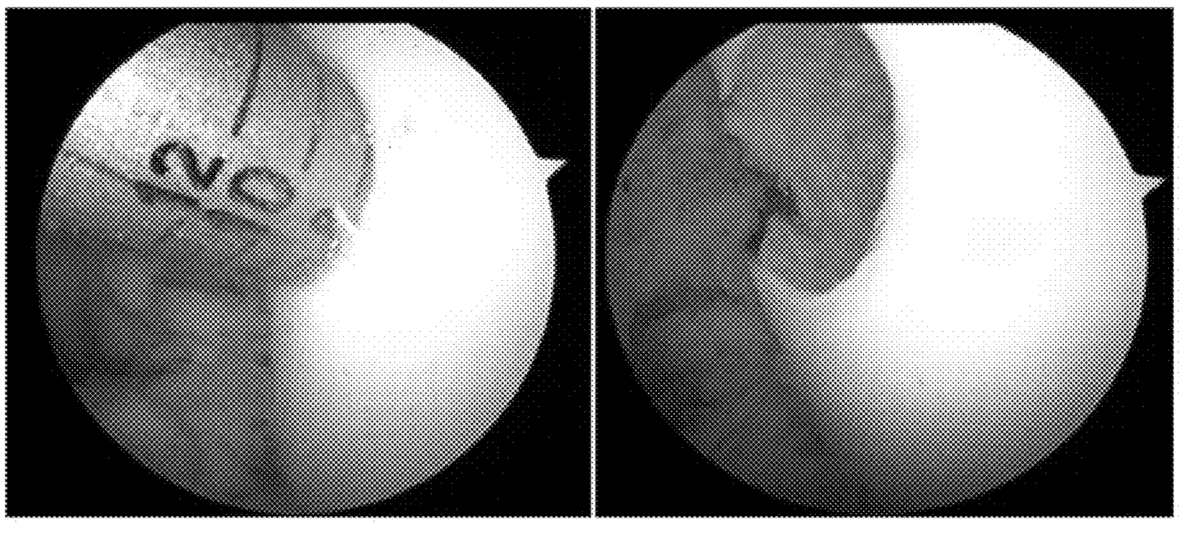
Figures 12C, 12D:
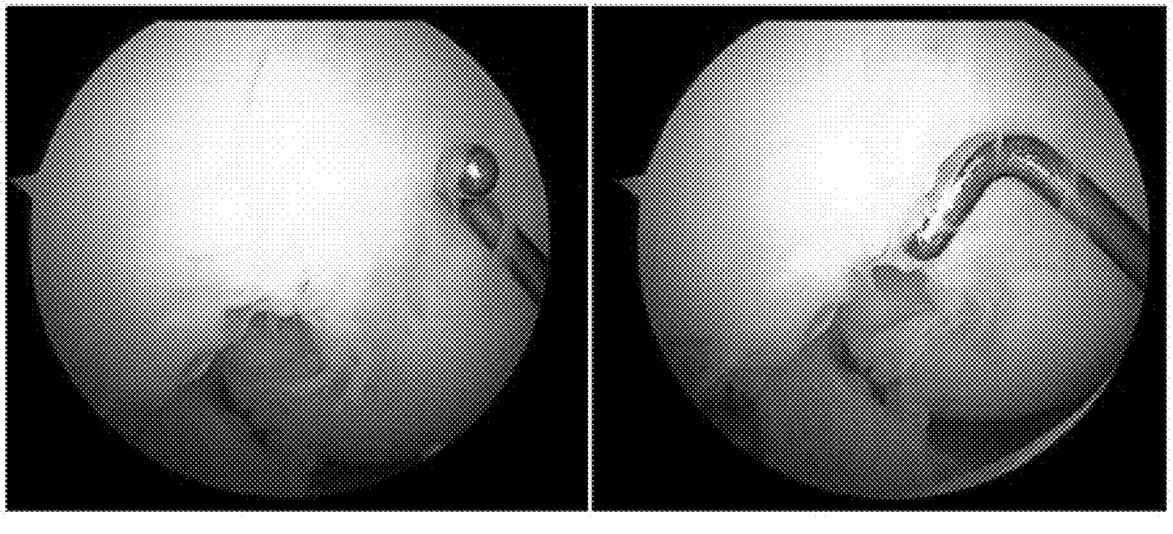
Figures 13A, 13B, 13C:
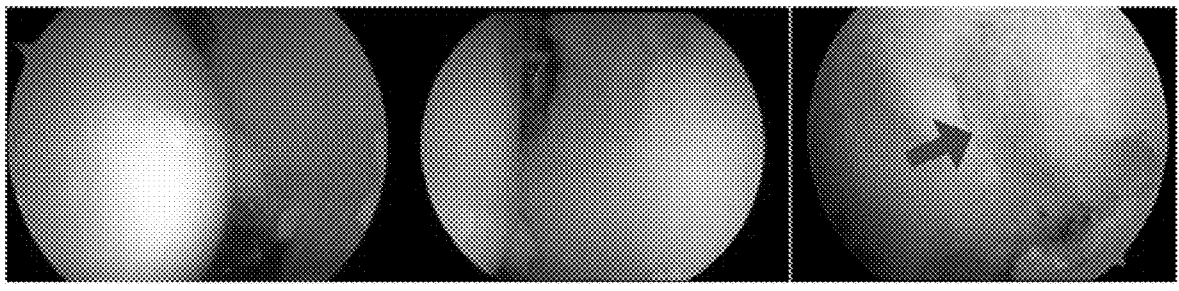
Figures 13D, 13E, 13F:
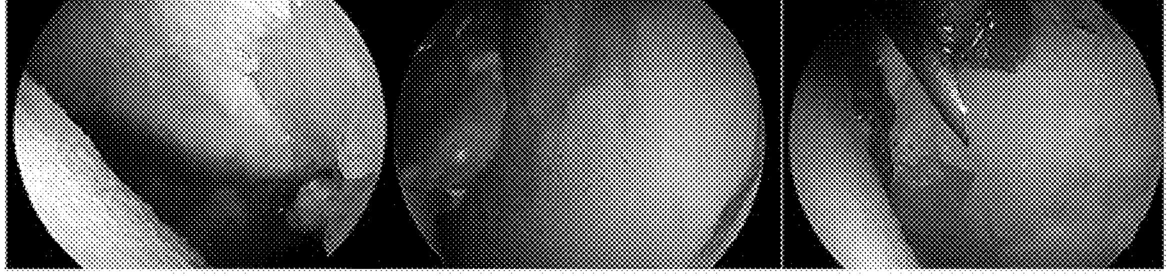

FIGS. 12A-12D. show a fibrocartilage formation at the donor site in the ICA. Arthroscopic evaluation of osteochondral biopsy sampling in autologous chondrocyte implantation (FIGS. 12A and 12B). Subsequently, a second arthroscopic view 12 months after the autologous chondrocyte implantation clearly shows filling of the donor area with abundant presence of fibrous, irregular and fibrillar tissue (FIGS. 12C and 12D).

FIGS. 13A-13F show a placement of hip construct. Left hip arthroscopy. In image 13A and 13B, the cartilage lesion is identified in the anterior-superior region of the acetabulum (25×10 mm), while in image 13C and 13D, a lesion of the same size but in the postero-superior area. Both lesions involve 40% of the total joint surface. Image 13E and 13F, show the placement of the allogeneic chondrocyte implant and its fixation with fibrin glue.

Figures 14A, 14B:
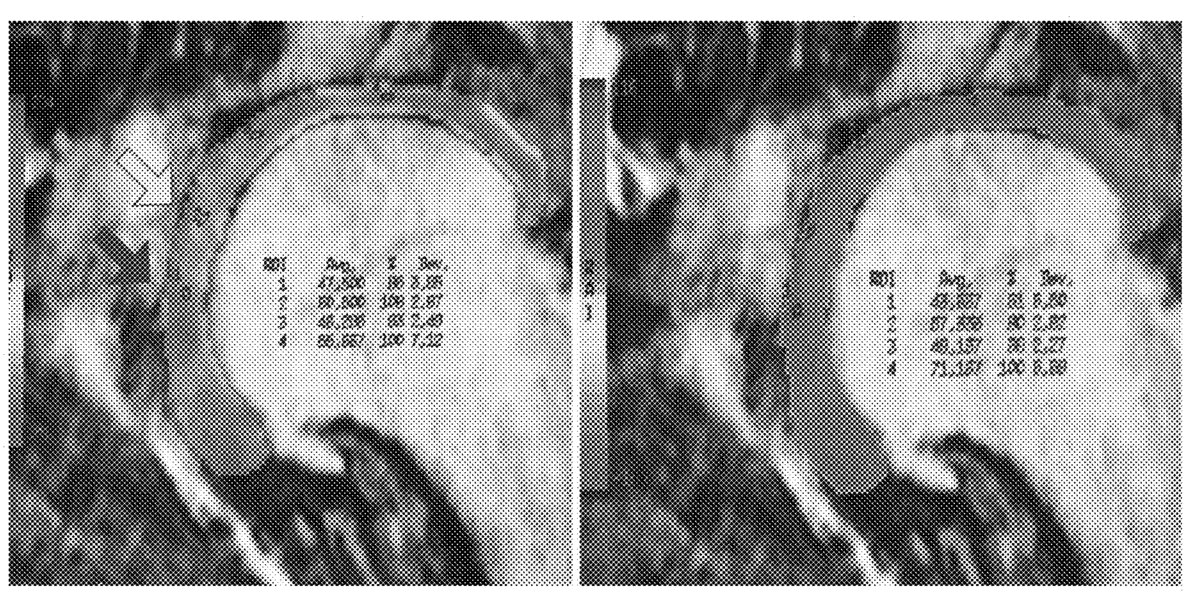
Figures 15A, 15B, 15C:
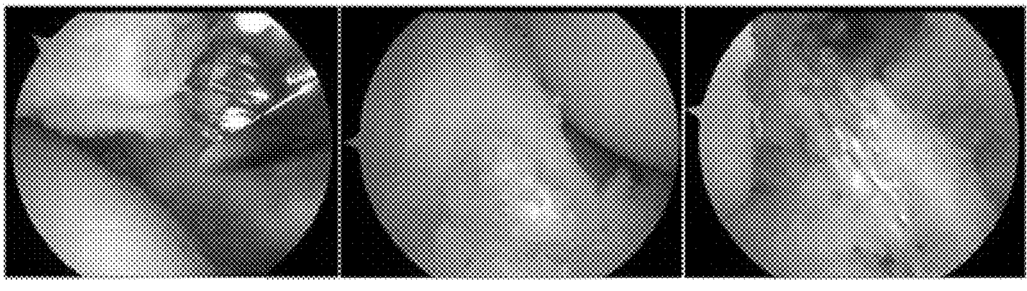
Figures 15D, 15E, 15F:
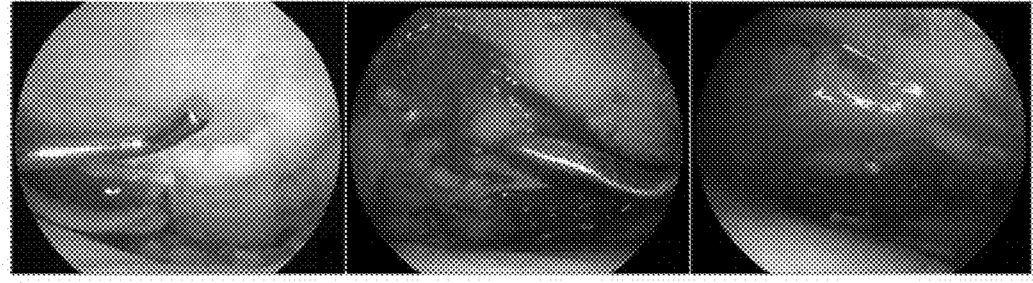

FIGS. 14A-14B show a quality of the cartilage repaired in the hip. Evaluation of the quality of the repair tissue by measuring the water relaxation time 3 months after hip implantation. The red arrow indicates the value of the control cartilage (ROI-1) versus the repair tissue measurement (ROI-2) (47.5 ms vs 50.5 ms), the values are very similar.

FIGS. 15A-15F show a knee construct placement. The figures show the placement of the graft with cadaveric chondrocytes in patella. 15A) Resection of bony prominence (osteophyte) to avoid erosion of the cartilage of the trochlea. 15B) Osteophyte at the base of the anterior cruciate ligament (ACL). 15C) ACL reconstructed with synthetic graft. 15D) Cartilage lesion on the lateral facet of the patella (30×30 mm). 15E). Placement of the graft or hyaluronic acid construct seeded with allogeneic chondrocytes in the area of the lesion. 15F) Application of fibrin glue to promote adhesion of the implant to the lesion and adjacent cartilage.

Figures 16A, 16B:
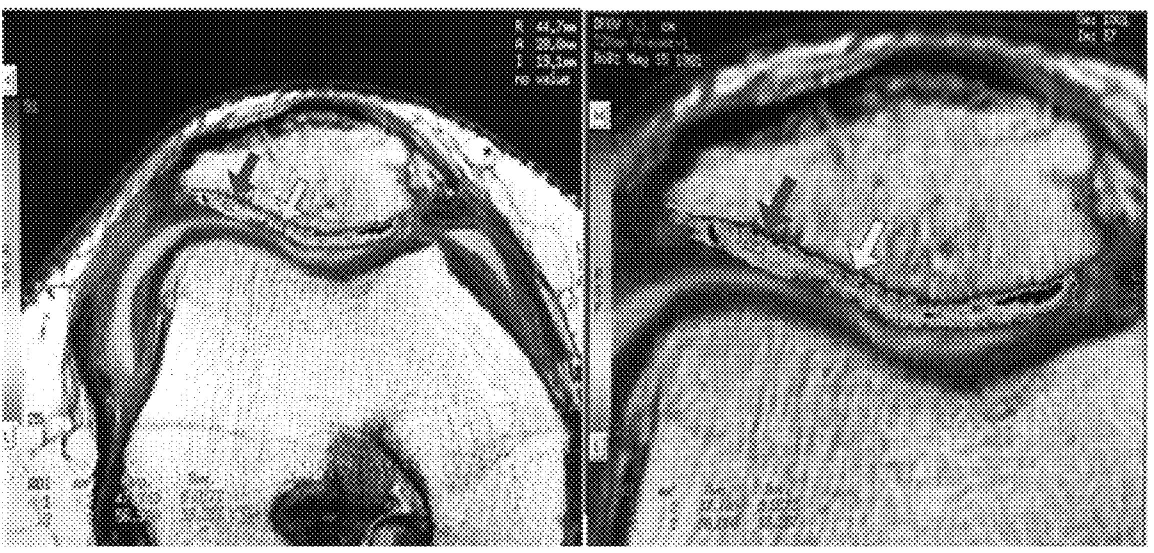

FIGS. 16A-16B show a quality of repaired cartilage in the knee. The figures show the evaluation of the quality of the repair tissue by measuring the water relaxation time 3 months after the knee implant. Red arrow indicates control cartilage value (ROI-1) versus repair tissue measurement (ROI-2) (47.7 ms vs 56.9 ms). The repair tissue value still reflects the presence of immature cartilage at 3 months.

Figures 17A, 17B:
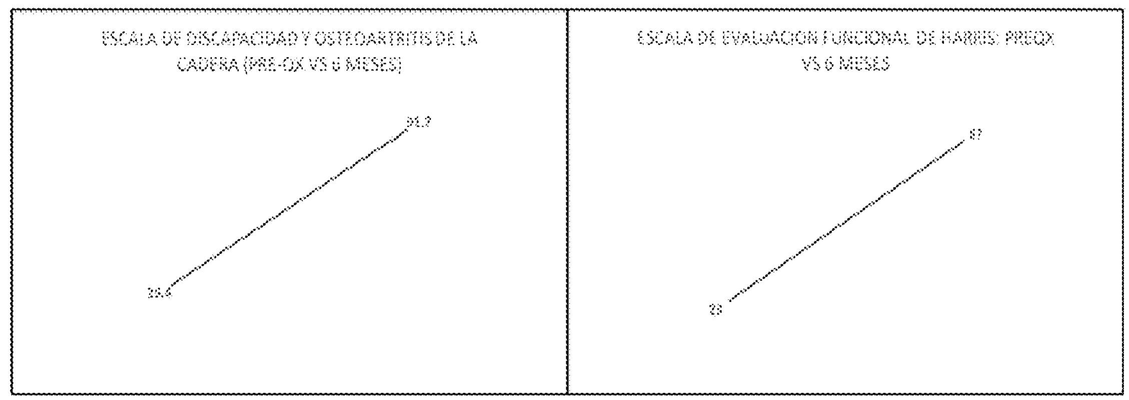

FIGS. 17A-17B show a functional hip assessment scales before and after surgery. Functional hip assessment was performed using widely recognized scales, for example the Harris hip scale is the most widely used instrument to evaluate the results obtained after hip arthroplasty. The evaluation was performed pre and post-surgery to assess the movements of the transverse, anteroposterior and longitudinal axes or arches of mobility.

FIGS. 18A-18E show a knee functional assessment scales before and after surgery. Functional knee assessment was performed using widely recognised scales such as the TEGNER scale, LYSHOLM, IKDC (International Knee Documentation Committee) and KUJALA. Evaluation was performed pre and post-surgery to assess arcs of mobility, pain and knee function.

DESCRIPTION OF THE INVENTION

The present invention refers to an implant or construct for the treatment of cartilage lesions in joints of an individual, wherein said implant is composed of allogeneic chondrocytes, derived from cadaveric donor, cultured on a hyaluronic acid scaffold, sealed with a biocompatible glue. Likewise, it refers to a kit for the treatment of cartilage comprising primary culture of allogeneic chondrocytes, derived from cadaveric donor, seeded on a hyaluronic acid membrane, and covered with a biocompatible glue, disposed in a container or container suitable for such purpose, wherein said container also comprises a culture medium, supplemented with autologous serum and antibiotic-antimycotics.

The invention of the present application, clearly contributes to solve at least one of the multiple latent inconveniences in the technical area, one of the great advantages of the present invention is that it favors the formation of a better quality of hyaline cartilage which favors the integration of the implant to the adjacent native tissue and we have also observed in all the treated patients that the risk of immunogenic reactions is diminished, since we have observed that all the patients submitted to this technique have not presented local or systemic data of rejection, such as: increase of articular volume, increase of the local temperature, absence of rejection or detachment of the implant when evaluated by magnetic resonance. Another of the great advantages of the present invention lies in the fact that from the donor tissue enough material is obtained to treat large lesions, that is to say, there is no limit to the number of cells to carry out the medical treatment. A further great advantage of the present invention is that the procedure for obtaining the graft or construct requires short times (approximately 1 week) in comparison with the various methodologies (approximately 8 weeks) described in the prior art. The present invention uses chondrocytes isolated from articular cartilage (knee and/or patella) from young donors (<20 years), seeded on a three-dimensional membrane, composed of one of the main chondrogenesis-promoting substances (hyaluronic acid), in high densities (1×106) with autologous serum and sealed with a fibrin adhesive.

In the present invention we have observed that in the development of the described implant it has been observed that the seeding of the chondrocytes on the membrane or scaffold has allowed to maintain a three-dimensional environment, which in turn is necessary to maintain in appropriate conditions the chondral cells and, in this way, prevent them from dedifferentiating to "fibrochondrocytes". It is highly desirable to avoid harvesting fibrochondrocytes, since the repair cartilage formed from these cells is of poor quality and durability, as these cells produce structural components very different from those of native hyaline cartilage. On the other hand, we have observed that the structural nature of the hyaluronic acid membrane allowed us to obtain an implant with the desirable flexibility and strength to be manipulated during arthroscopy. Likewise, during the development of the present invention and with the described methods, we found that more than 80% of the chondrocytes obtained from cartilage, coming from cadaveric donor knees, up to 48 hours after death, maintain their viability and preserve the capacity to form cartilage in in-vitro cultures (FIGS. 4A-4D and 5A-5D).

For the purposes of the present invention, the terms or expressions "construct", "graft", "chondrocyte graft", "chondrocyte graft", "implant", "chondrocyte implant" or "orthopedic implant" are used interchangeably with the same meaning and scope of protection. In these we refer to a cartilage substitute with the ability to repair, regenerate or replace functionally and structurally cartilage in a patient who has lost the function of such tissue, or when such tissue has suffered some mechanical or physiological damage.

For the present invention the expression "cadaveric donor" refers to the cartilage tissue being derived from a deceased donor, wherein said donor is approximately 20 years of age or less, preferably less than 20 years of age at the time of donation. Normally, chondrocytes derived from a young individual present a greater capacity to synthesize/organize the extracellular matrix of hyaline cartilage vs those chondrocytes derived from an adult individual.

For the present invention the expression "allogeneic chondrocytes" takes the conventional meaning in the technical area, which refers to chondrocytes from different individuals of the same species.

For the present invention the terms or expressions "membrane", "scaffolding" or "support" are used interchangeably with the same meaning and scope of protection. In these we refer to a support structure, made up of one or more materials of different nature, preferably biocompatible, resorbable and resistant materials. This membrane provides a mechanical support on which the chondrocytes are deposited, which facilitates their placement at the site of the defect to be treated, and also allows these cells to remain at the site of the defect. In one embodiment the membrane is composed of a layer of a synthetic biopolymer of hyaluronic acid or derivatives thereof, in particular esterified derivatives, furthermore it does not contain animal or human by-products, which avoids allergic reaction of other products. In another modality, the membrane is composed of a layer of a synthetic biopolymer of hyaluronic acid esterified with benzyl alcohol and some of its characteristics are: it is biodegradable, mechanically resistant, biocompatible, non-cytotoxic (does not destroy cells), non-antigenic (does not cause immune response), promotes cell proliferation and differentiation, is flexible and elastic, and allows the passage of nutrients and metabolic waste and its mechanism of metabolization is known and safe. This membrane is degraded through hydrolysis (decomposition by water) of the ester, resulting in the release of HA and benzyl alcohol.

For the present invention the term or expression "fibrin tissue adhesive" or "fibrin glue" refers to cellular adhesive compositions based on human fibrinogen and thrombin, which allows to generate a fibrin clot for hemostasis, sealing and healing of tissues and for improving tissue adhesion. In one embodiment, it is desirable that such adhesive contain only components of animal or synthetic origin, in order to avoid adverse reactions to the adhesive by the recipient organism. In another embodiment, the adhesive may contain other components, other than those previously mentioned, to strengthen its adhesive property. In another modality, the fibrin adhesive can be obtained from autologous serum during surgery, or one of synthetic origin and of commercial use. Some of the fibrin-based adhesive products that are commercially available are, for example: Beriplaste® Behering, Tisseel® from Baxter, Evicel® from J&J, etc.

For the present invention the term or expression "culture medium" or "medium" refers to compositions suitable for the culture of chondrocytes, since they support or favor the maintenance and/or growth of the cells in culture in vitro. In some preferred embodiments, it also refers to the culture medium supplemented with one or more additional components. In some embodiments, the additional components can include, for example, serum, antibiotics, antifungals, growth factors, buffers, pH indicators, and the like. In other embodiments, the medium can be used in the process of isolating cells (e. g., chondrocytes and/or chondrocyte precursors) from a tissue sample (e. g., a cartilage sample). In some embodiments, tissue is mechanically digested and then subjected to enzymatic digestion, combined with medium that may comprise enzymes (e. g., collagenase or protease) to digest tissue and release cells.

For the present invention the term or expression "allogeneic cadaveric chondrocytes" or "cadaveric chondrocytes" refers to chondrocytes that are isolated from cartilage derived from young cadaveric donors, up to 20 years of age. In some embodiments, the isolated cells can be used immediately, or cryopreserved, without expansion (P0), until use.

EXAMPLES

The present examples are of an illustrative and non-limiting nature, since a person skilled in the art will understand that there are variants which fall within the scope of protection of the present invention.

Example 1: Obtaining Cadaveric Chondrocytes

Selection of Cadaveric Donors

For the present invention the biopsies or tissue sample is obtained from healthy young donors. In one modality, donors are selected from the male gender, to avoid hormonal variables in the biology of the chondrocytes obtained. Young donors are selected from an age of up to 20 years old, in one modality they are selected with an age between 14 and 20 years old. The cartilage samples are obtained from the knees of the donors (see FIGS. 2A-2F), taking as an important factor that they are macroscopically healthy joints (without evident presence of traumatic cartilage lesions, crystal deposits, degenerative chondral lesions, previous or active infection and/or rheumatological diseases). So, the staff that procures the tissue corroborates that the tissue is smooth and whitish.

In one embodiment, the biopsies or tissue samples used in some of the examples of the present invention were provided by the Biograft Musculoskeletal Tissue and Skin Bank of Mexico.

Donor Serology Panel

Once a cadaveric donor is selected and a biopsy or tissue sample is taken, this tissue is subjected to a panel of studies to rule out the presence of infectious diseases that can be transmitted through the donated tissue. The panel includes the study of antibodies against hepatitis B (Core and Surface), hepatitis C, HTLV, syphilis, HIV and detection of nucleic acids (NAT test) against hepatitis B, C and HIV. Once biopsies or tissue samples report negative serology they are considered suitable for use in the formation of the implant or construct of the present invention.

In one embodiment of the present invention, some of the biopsies or tissue samples used in the present invention were sent to the Viromed/Labcorp laboratory, in Minnesota, United States, who performed said panel of studies.

Obtaining the Biopsy

Once a tissue donor with the described inclusion criteria is identified, the tissue procurement staff plus an orthopedist expert in the collection of cartilage go to the hospital where the death occurred, under aseptic, sterile conditions, they proceed to perform the arthrotomy of both knees and to collect cartilage fragments (see FIGS. 2A-2D), which are placed in sterile containers (FIG. 2E-2F), containing culture medium (DMEM-F12) supplemented with 10% antibiotic-antimycotics, then transferred to −4° C. to the laboratory of the Tissue Bank (Biograft) to be processed.

In one embodiment of the present invention cartilage samples are taken from femoral condyles and patella (FIGS. 2A and 2B), using a scalpel, with #20 blades. The tissue is taken from the most superficial part (FIGS. 2C and 2D), with the purpose of not deepening the cut to the subchondral bone, to avoid the exit of bone marrow stem cells and contact with intramedullary fluids or contamination of the tissue with cells of another origin.

At the biopsy procurement site, donor data are documented to standardize characteristics that may influence the viability and chondrogenic capacity of the cells (age, gender, associated pathologies and cause of death). Likewise, associated variables such as time of death and time between death and cartilage harvesting are also verified.

Isolation of Chondrocytes

Isolation of chondrocytes (see FIGS. 3A-3E) is carried out in appropriate facilities for this purpose, for example, in a tissue culture laboratory, under sterile conditions and in a level II laminar flow hood. The tissue is washed, with PBS+10% antibiotic-antimycotic, at least a couple of times or more to remove donor fluids and debris, in one modality 3 or more washes are preferred. The cartilage obtained is weighed and the ratio of the number of chondrocytes obtained per milligram of tissue is obtained.

Subsequently, a mechanical digestion is performed, to obtain cartilage fragments smaller than 1 mm (see FIG. 3B), followed by an enzymatic digestion with collagenase-type 2 (0.1 to 0.3% w/v), for at least 1 hour at 37° C., under continuous agitation; in one mode the digestion is carried out for at least 2 hours, in another equally preferred embodiment the digestion is carried out for at least 3 hrs, in another equally preferred embodiment the digestion is carried out for at least 4 hrs. As it is evident, the efficiency of the enzymatic treatment can be obtained with the variation of different parameters, for example, the efficiency increases when there is a greater surface of the exposed tissue, when the quantity or activity of the enzyme is increased and with the digestion time. The enzymatic digestion could be carried out continuously or, alternatively, be carried out in two or more digestion steps; for example, the digestion is carried out for 60 to 120 minutes, the supernatant containing the cells released by the digestion is recovered, and the undigested fragments are subjected to a second digestion step with a fresh enzyme solution for at least another 60 to 120 minutes (FIG. 3C).

Cell number and viability are determined by counting in Neubauer chamber and trypan blue (FIG. 3D). The obtained chondrocytes are cryopreserved (FIG. 3E) without expanding, in order to preserve and maintain their viability, morphology and functionality, several methodologies are known in the state of the art for this purpose. The cryopreservation medium comprises culture medium, serum or combinations thereof and a cryoprotectant substance. In one embodiment, the cryopreservation or freezing medium may be composed of 10% commercial human serum or 10% autologous serum, although autologous serum is preferred, plus 80% DMEM/F12 culture medium and 10% DMSO. DMSO is a cryoprotective substance that prevents chondrocytes from swelling and bursting upon freezing. In one embodiment of the present invention, the chondrocytes obtained were deposited in the above-mentioned freezing medium in a vial in which 1 ml of said substance was deposited for a maximum of 500,000 cells and stored in a liquid nitrogen chamber at −192° C.

Example 2: Formation of the Implant or Construct

Autologous Serum

A sample of peripheral blood (200-250 ml) from the patient to be treated is processed by centrifugation to remove the red fraction and obtain the autologous serum, which is inactivated, filtered and aliquoted in 10 ml tubes and stored in sterile conditions at −4° C., until its use is required.

In one modality, the orthopedic surgeon, who requests the graft, provides the tissue culture laboratory or tissue bank with the data of the patient to be treated, who is contacted to donate a sample of peripheral blood (200-250 ml), to obtain the autologous serum, preferably 5 to 7 days prior to surgery.

Preparation of the Implant

To prepare an implant or construct, the chondrocytes are thawed, through a gradual process to minimize the percentage of cell death and, once thawed, the cell viability is counted and determined again. Next, the chondrocytes are seeded on the hyaluronic acid membrane or scaffold at a density of 1×106 cells per cm2. The construct is sealed over its entire surface with fibrin glue to promote adhesion of the chondrocytes to the membrane and decrease the risk of cell loss. The size of the hyaluronic acid membrane or scaffold, in one modality the hyaluronic acid is of synthetic origin, is a function of the requirements of the orthopedic surgeon who will implant it, and can range in size from 10×10 mm to 50×50 mm. The membrane-seeded chondrocytes are cultured at 37° C., 5% CO2 and 5% humidity, with DMEM-F12 culture medium+10% autologous serum+1% antibiotic-antimycotic. The culture medium is changed every second or third day for a period of 5 to 7 days (FIG. 4), to allow cell adhesion and the formation of extracellular matrix. The autologous serum is obtained from the patient to whom the construct is to be implanted, thus avoiding the use of fetal bovine serum which may cause secondary reactions in the patient.

Example 3: Evaluation of the Presence of Proteoglycans in the Formed Cartilage During the development of the invention, tests were performed on the viability of chondrocytes obtained from cadaveric donor (P0), as well as on their ability to form hyaline cartilage. These were subjected to comparative studies with chondrocytes obtained from living donor without expansion and without cryopreservation (P0) and chondrocytes obtained from living donor expanded, during 2 passes, without cryopreservation (P2), in both cases the donors presented similar demographic conditions. For all groups, chondrocytes were seeded on a collagen membrane, subsequently this implant or construct was implanted in the dorsum of athymic mice (Nunu), which were monitored for 3 months. At three months, the tissue formed in each of the study groups was evaluated by staining and immunofluorescence for cartilage and compared with native hyaline cartilage.

The tissue formed in the different groups was analyzed by staining with alcian blue (blue staining) and Safranin-O (red-brown staining). Alcian blue staining highlights cartilage and is especially useful for differentiating articular hyaline cartilage vs. bone, since the cartilage extracellular matrix stains with alcian blue (FIGS. 5A-5D). On the other hand, staining with Safranin-O dye has become a basic guide in the identification of articular cartilage, because safranin-O binds to glycosaminoglycans (GAGs), which are terminal structures of proteoglycans such as aggrecan, which is an essential component of articular cartilage and abundant in the extracellular matrix of articular cartilage. It is also considered that the intensity of safranin-O staining is directly proportional to the content of PG in cartilage (FIGS. 6A-6D).

Figure 1:
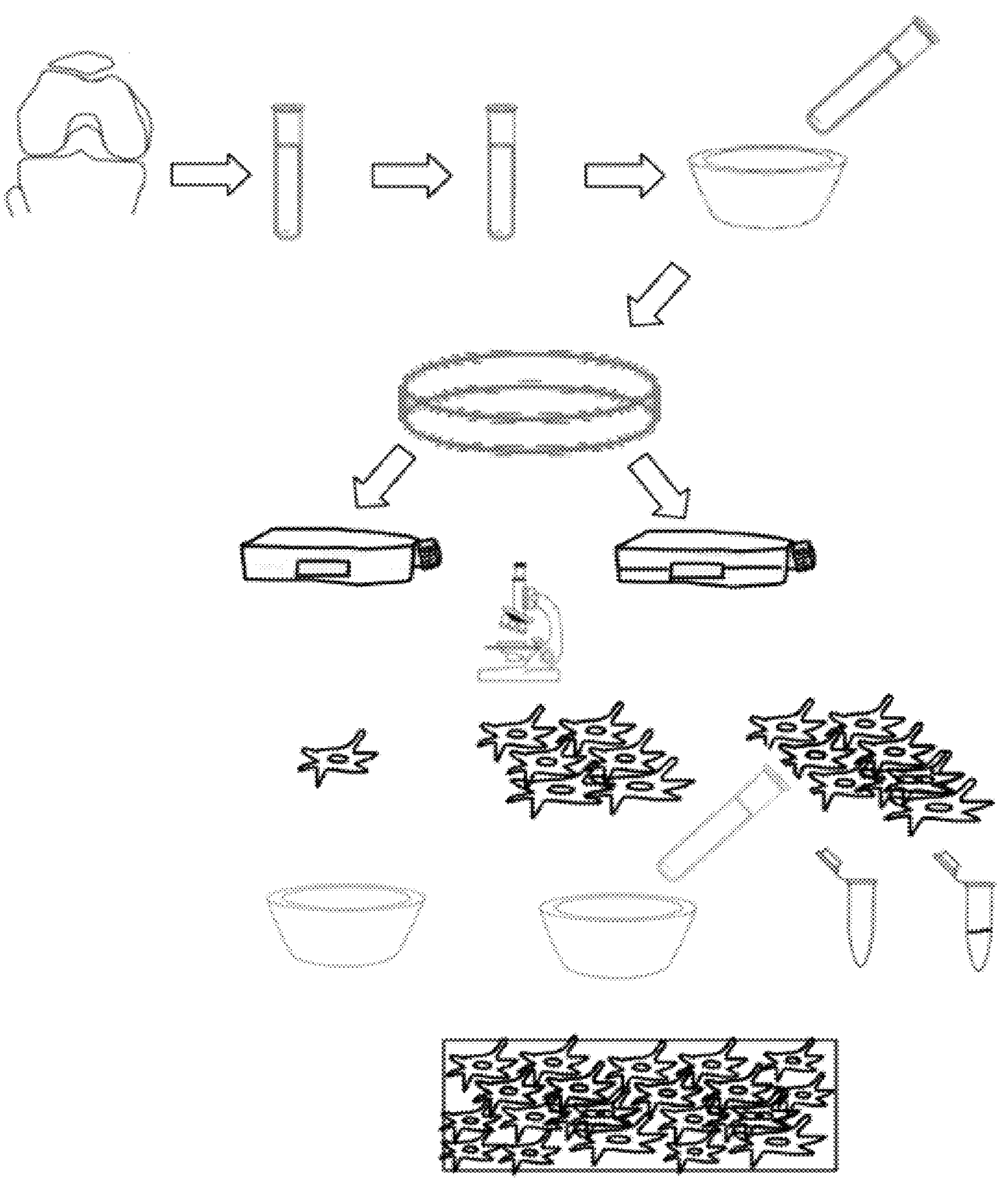
FIG. 1 shows a flow diagram of the method of obtaining the implant or construct with allogeneic chondrocytes of the present invention.
Figures 2A, 2B, 2C:
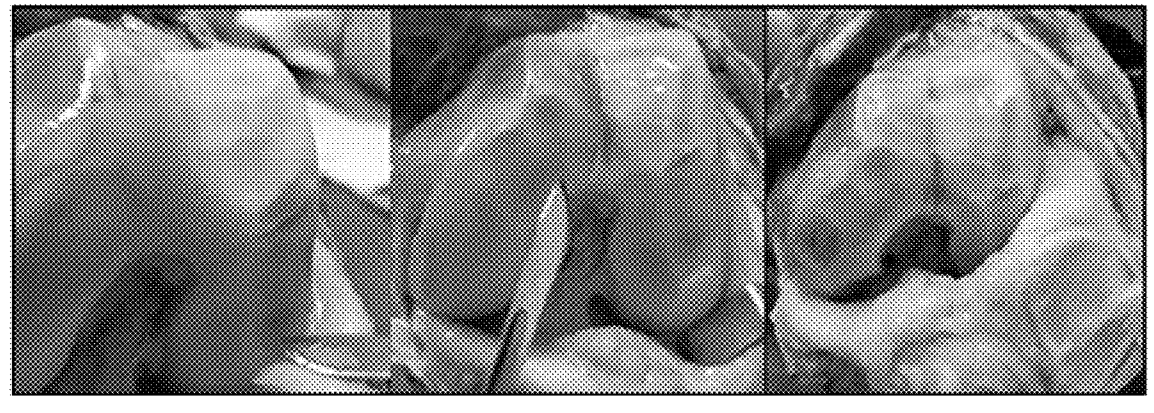
FIGS. 2A-2F. Procedure for obtaining cartilage biopsies from cadaveric donor. In one embodiment of the present invention cartilage samples are taken from femoral condyles and patella (FIGS. 2A and 2B), using a scalpel, with #20 blades. The tissue is taken from the most superficial part (FIGS. 2C and 2D), with the purpose of not deepening the cut to the subchondral bone, to avoid the exit of bone marrow stem cells and contact with intramedullary fluids or contamination of the tissue with cells of another origin.
Figures 2D, 2E, 2F:
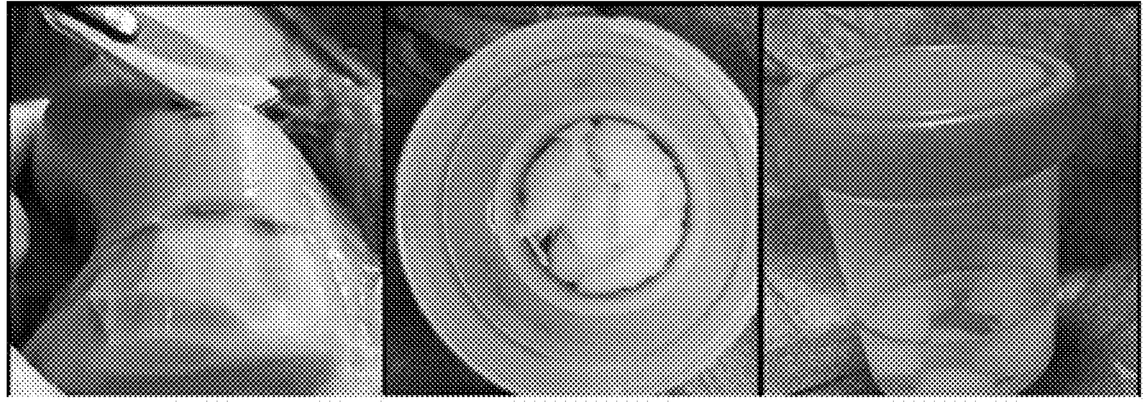
Figures 5A, 5B:
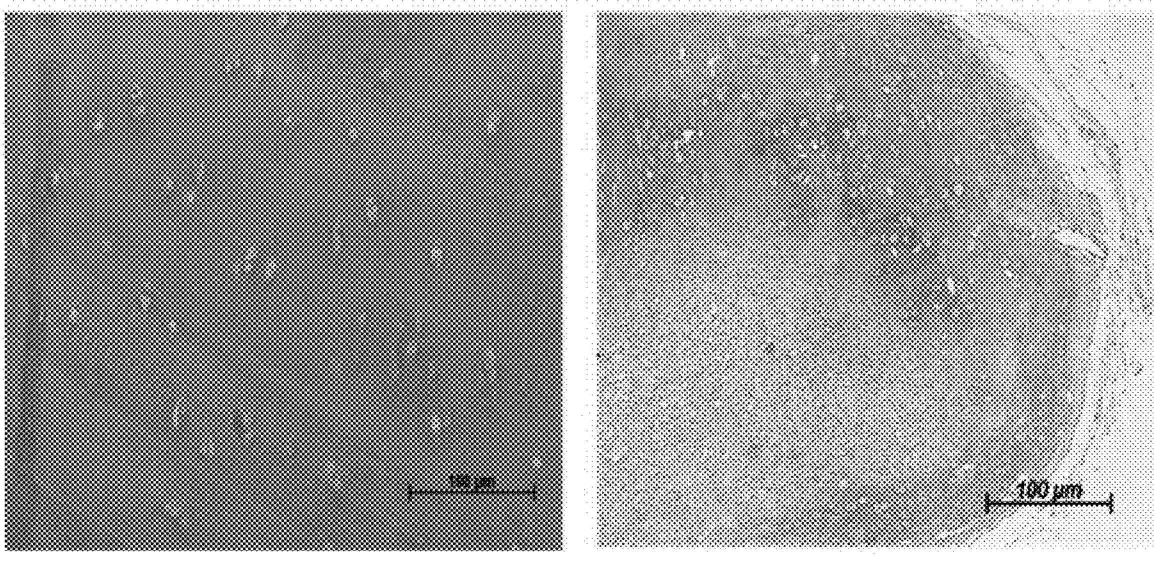
Figures 5C, 5D:
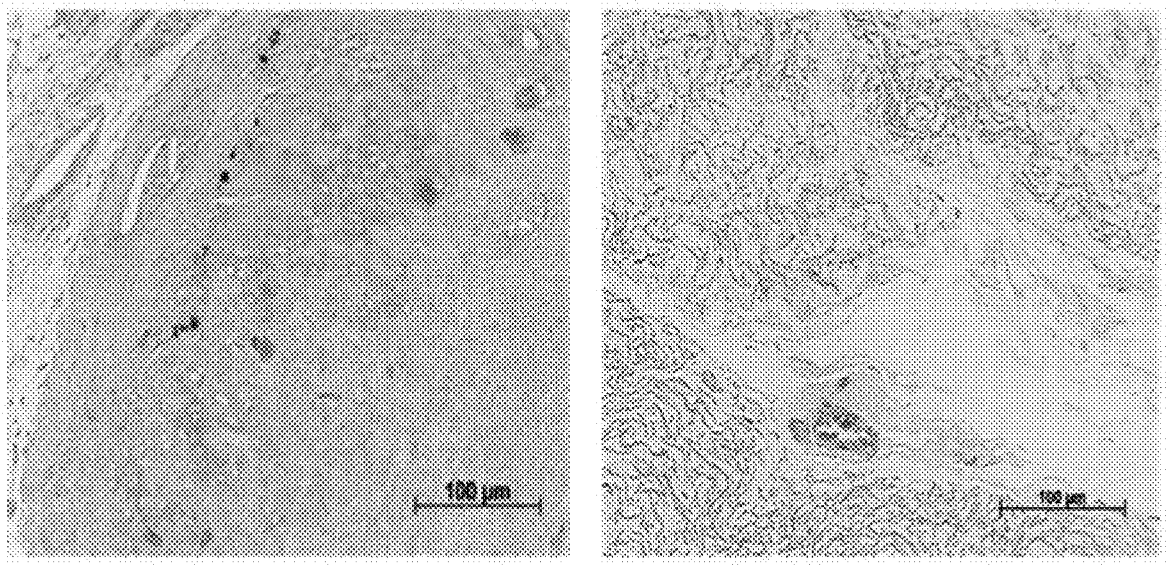
Figures 6A, 6B:
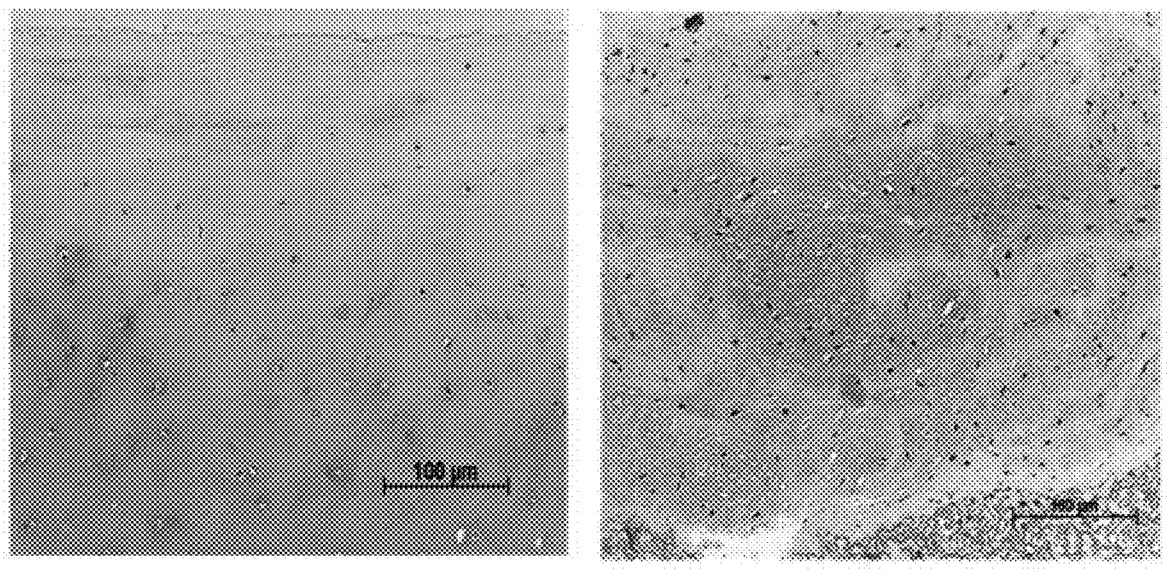
Figures 6C, 6D:
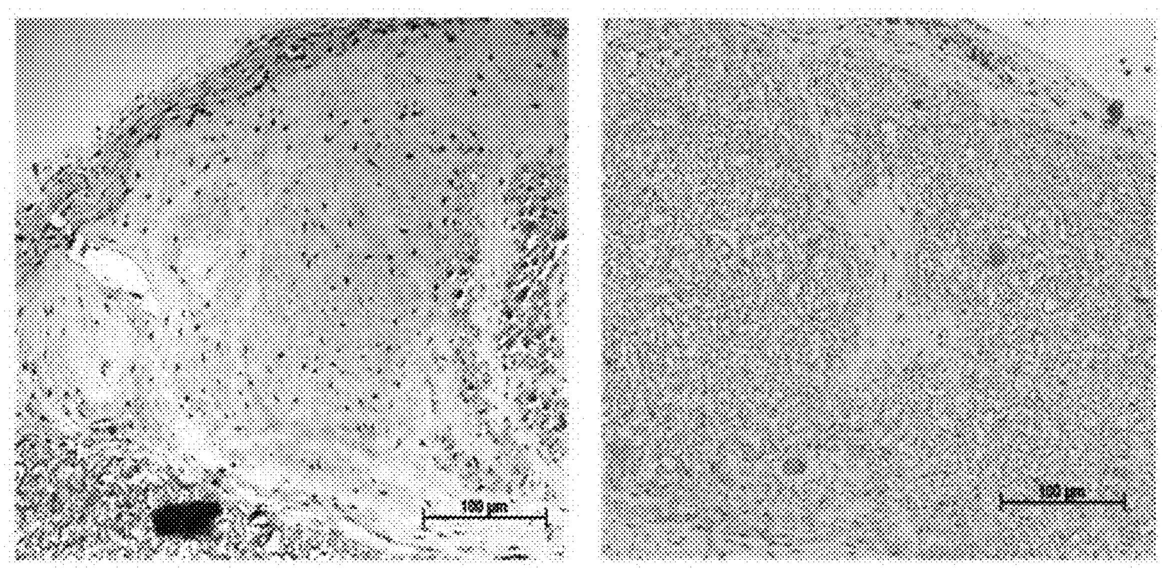

The results are shown in FIGS. 5A-5D, where histological sections stained with alcian blue are observed. In (5A) the control tissue, native hyaline cartilage, is shown; in (5B) tissue generated from cadaveric chondrocytes (P0) of the present invention is observed, while in (5C) and (5D) tissue generated from living donor-derived chondrocytes (P0 and P2, respectively) is observed. The images clearly show that tissues generated from living donor chondrocytes (FIGS. 5C and 5D) exhibit moderate to very low staining, respectively, while tissue generated from cadaveric chondrocytes (P0) of the invention exhibit very pronounced blue staining (FIG. 5B). This blue staining allows to identify an extracellular matrix, of homogeneous aspect, characteristic of hyaline cartilage, the extracellular matrix is secreted by the chondrocytes generated from the implant or construct of the present invention. In addition, FIG. 5B clearly shows the chondrocytes that are usually associated in pairs or tetrads, thus forming the so-called isogenic groups.

Likewise, from this result it can be seen that the chondrocytes of living donor (P2), which were cultured during 2 passages (FIG. 5D) practically lose the capacity to generate articular hyaline cartilage vs. the control tissue of the histological section (FIG. 5A). Even more important is the result derived from the comparison of figures (B) vs (C), in which the tissue formed from the cadaveric chondrocytes of the present invention (P0) vs healthy donor chondrocytes (P0) is observed, under the same conditions; it is evident that when the implant or construct of the present invention is used, hyaline cartilage formation is induced, which is evidenced by the marked alcian blue staining that evidences the formation of extracellular matrix.

Example 4: Quantitative Evaluation of the Quality of Formed Cartilage

A quantitative analysis of the histological staining was carried out by three independent and blinded observers, using the modified O'Driscoll histological scale, which evaluates the percentage of cartilage formation, the quantity and quality of the cells formed and the structure of the tissue. In this evaluation, a maximum score of 14 points is given to the native cartilage (FIGS. 6A-6D); the closer the score is to 14, which is assigned to the histological samples, the higher the quality of the formed tissue and the closer it is to healthy cartilage. Quantitatively, the tissue formed by the cadaveric chondrocytes (P0) that were cryopreserved without expanding, of the present invention, obtained a mean of 9.57 (SD1.27). On the other hand, the cartilage formed by living donor chondrocytes (P0) that were not expanded and were not cryopreserved, obtained a score of 8.71 (SD3.98), with no significant difference with cadaveric chondrocyte tissue ($p<0.05$).

However, with the present invention the source of obtaining the chondrocytes becomes significantly important when considering that when chondrocytes are obtained from a cadaveric donor, the requirement of performing a first surgery on the patient to be treated is eliminated, thus avoiding the risks of morbidity in the donor area and significantly decreasing the costs and times of treatment and recovery. Likewise, another great advantage is that from the cadaveric donor source a greater amount of tissue is obtained and thus a greater amount of cells for implants or constructs, which eliminates the need for prolonged cultures that carry the risk of generating fibrocartilage instead of hyaline cartilage, this also allows to treat lesions of any size, this also impacts on treatment costs and one of the most important aspects is that it allows the generation of a tissue more similar to hyaline cartilage compared to that formed with living donor chondrocytes, which are not cultured or cryopreserved.

Implants or constructs of living donor chondrocytes, which were cultured for 2 passages (P2) formed a tissue with little resemblance to cartilage, on the contrary, presented a much more fibrous appearance vs hyaline cartilage, probably this is due to the dedifferentiation that undergo chondrocytes to be expanded several times in monolayer cultures. The mean score of this group on the O'Driscoll scale was 4.37 (SD4.7), clearly indicating that the tissue formed has characteristics far removed from hyaline cartilage.

1 contrasts the differences between the traditional technique (ACI) versus the proposed innovation (ALCI).

TABLE. 1

Technical advantages of the invention vs. traditional technique.

| ACI | ALCI |
|---|---|
| Cartilage taken from the knee of the same patient | Does not require removal of cartilage from the patient to be treated. |
| Two surgeries (biopsy and implant placement) | One surgery (implant only) |
| In-vitro culture for 6 to 8 weeks. | Cultivation 1 week |
| Multi-pass culture causes chondrocytes to become fibrocytes (produce fibrosis vs. cartilage, which results in early failure). | It does not require any passaging during culture, thus eliminating the risk of cell dedifferentiation. |
| Higher cost per prolonged culture Material, facilities and trained human resources: $250,000 Mx per patient | Short culture with estimated cost reduction of up to 70% for each patient ($75,000 Mx). |
| Technique limited to people <50 years of age | There is no limitation on the age of the patients to be treated. |
| Decreased ability to form cartilage Repair tissue is of low to very low quality. | Because the tissue is derived from young, healthy donors Formation of better quality cartilage |
| Accessible to specialized centers with laboratories designed for such cultures and patients with high financial capacity. | Accessible to any patient and hospital with a standard operating room and an orthopaedic surgeon trained to perform knee surgery |

En el implante de condrocitos autólogos (ACI), la fuente de cartílago es muy limitada ya que provienen del mismo individuo, por esta razón resulta obligado cultivar las células, por lo menos durante dos pases (8 semanas), para expandirlas con el propósito de incrementar el número de células, para poseer suficiente cantidad de células para la reparación de una lesión de cartilago. Con los resultados obtenidos (FIGS. 5A-5D and 6A-6D) presentados previamente, se demuestra que existe un riesgo muy alto, prácticamente inaceptable, de que los pacientes tratados con esta técnica generen fibrocartílago, con el consecuente riego de falla prematura, lo conveniente es que se forme un tejido lo más parecido a cartílago hialino, como se demostró en la presente invención.

Allogenic Chondrocyte Implantation (ALCI) is a technique that, like Autologous Chondrocyte Implantation, repairs a joint injury with tissue very similar to native cartilage, reducing treatment times, costs, number of surgeries, affectation in the donor site of autologous cartilage, greater availability of the amount of cells required to treat an injury of considerable size, elimination of the need to cultivate and expand the chondrocytes in the laboratory, selection of chondrocytes from young cadaveric donors to improve the quality of the tissue formed. This invention allows a high availability of cadaveric chondrocytes, which allows them to be used at any time and in any place required (any hospital in any state of the Mexican Republic and even to be marketed internationally). This availability as an implant or construct elaborated in the tissue bank eliminates the need for the hospital center, where the patient is to be treated, to have a laboratory and/or sophisticated equipment to process the sample, so that the treating physician only has to request it from the tissue bank.

The quality of the repair tissue formed in a cartilage lesion depends on many factors that are covered with this innovation such as the seeding of cells in a three-dimensional hyaluronic acid membrane (forms better tissue than without scaffold), the number of cells that are implanted in the lesion (the more chondrocytes, the better tissue; characteristic that is not available when it comes to autologous chondrocytes), age of the donor (the younger, the better quality and greater durability of the tissue formed). In the traditional ACI technique, it is difficult to cover the last two aspects. Table 1 contrasts the differences between the traditional technique (ACI) versus the proposed innovation (ALCI).

Example 5: Implantation of the Implant or Allogeneic Chondrocyte Construct

The product of the present invention is useful for the treatment of cartilage lesions of any joint, in a preferred mode it is used for the treatment of knee cartilage lesions.

The product is provided as a kit comprising a sterile culture box, which in turn contains the implant or construct with culture medium, autologous serum, antibiotic-antimycotic; where the implant consists of a hyaluronic acid membrane, with dimensions ranging from 10×10 mm to 50×50 mm, where the allogeneic cadaveric chondrocytes are attached, at a density of 1×106 cells per cm2, covered with a layer of a fibrin cell adhesive. Once the graft or construct has 7 days of in-vitro culture, it is transported, under sterile conditions, to the hospital where the surgery will be performed.

In one embodiment of the present invention, the tissue engineers from the tissue bank laboratory (Biograft) attended the hospital to deliver the graft or construct and remained at the surgical procedure until the implant was placed. In another realization or modality, there is also the assistance of an orthopedic surgeon specialized in arthroscopy and sports injuries, expert in cartilage repair, for support and advice during the surgical procedure of orthopedists who are not familiar with the technique. The kit containing the graft of the present invention has been used by an orthopaedic surgeon by means of open surgery or minimally invasive surgery (arthroscopy) in an operating theatre, under sterile conditions. In this regard, it is recommended that prior to the use of the implant, the treating physician should evaluate the injury during surgery, identifying the location (femoral condyle, patella or trochlea) and size.

In order to have a good integration of the graft or construct of the present invention, it is recommended that, before the placement of the product, an adequate debridement of the lesion is performed (FIG. 8A and FIG. 8B) removing all damaged tissue and leaving stable edges of healthy cartilage (FIG. 8C). It is important that after debridement the lesion is measured again, as it is very certain that the size of the lesion is now larger than it was initially, i. e. before removal of the injured and unstable edges. If the surgery is open, the measurement can be made with a surgical ruler; if the procedure is arthroscopic, the hook probe, or a flexible ruler, is used to determine the exact size of the lesion in the proximal-distal and medio-lateral planes (FIGS. 8D and 8E). Likewise, it is highly recommended that the lesion be given a square or rectangular shape (FIG. 8F), to facilitate measuring and matching the size and shape of the product. It is equally important not to damage the subchondral bone.

Once the final lesion measurements are obtained, after debridement of the lesion, it is recommended to trim the graft or construct with an excess of at least 2 mm at each edge, preferably at least 5 mm more than the estimated measurement. It is preferable to have a larger construct, which can be compressed and adapted to the lesion, than to leave a fair or smaller construct, with the consequent risk that one or more of its ends will fail to integrate with the edges of the healthy cartilage.

The product can be fixed by any means suitable for the purpose, e. g. by means of biodegradable anchors or fibrin glue. In a preferred modality he recommends the use of fibrin glue, as it is less invasive, less expensive and much easier to place. For fixation with anchors, the exposed bone in the lesion must be perforated and an anchor placed for every 10 mm of lesion, the sutures are recovered and through them the construct is slid to the lesion already debrided, finally knots are tied to secure the fixation.

At the time the construct was placed in the lesion, water entry into the arthroscopy was closed to prevent loss of chondrocytes. A cannula was placed in the portal of best access to the lesion, and through this the construct was introduced into the joint (FIG. 9A), was placed and spread over the entire surface (FIG. 9B) until the lesion is completely covered and ensuring contact of the graft with all edges of the adjacent native cartilage (FIG. 9C). Finally, fibrin glue was applied to the edges and surface of the construct to ensure fixation of the implant to the lesion, (FIG. 9D). The knee should remain in extension for at least a couple of days to allow the product to adhere to the subchondral bone and adjacent cartilage edges.

Example 6: Evaluation of the Integration of the Construct by Means of MRI

In the present invention the nuclear magnetic resonance study was used, an imaging technique that is widely used to evaluate the integration of the construct in the defect area, in the follow-up of a patient, treated with the implant of the present invention. FIG. 10 shows the images obtained by MRI at 3 and 6 months postoperatively, respectively (FIG. 10A & FIG. 10B), in these it is clearly observed that from 3 months postoperatively there is a good integration of the graft and at 6 months there are changes in the intensity of the construct which reflects the presence of extracellular matrix formation by the seeded chondrocytes, as well as integration to the subchondral bone and adjacent cartilage Example 7: Repair of Cartilage Injury at 12 Months: ACI Vs. ALCI FIGS. 11A-11F show the arthroscopic evaluation 12 months after treatment of a cartilage lesion in the lateral trochlea of both knees in the same patient. In this patient, the right knee (FIGS. 11A, B and C), with a 20×15 mm lesion, was treated with autologous chondrocyte implantation (ACI); in this case, repair tissue with 80% partial-thickness filling was observed (FIG. 11A), with irregular surface, predominant presence of fibrocartilage (FIG. 11B) and fibrillation zones (FIG. 11C). In contrast, the left knee (FIGS. 11D, E and F), with a lesion of 18×15 mm, was treated with the allogeneic chondrocyte implant of the present invention (ALCI), in which repair tissue with 95% partial thickness filling was observed (FIG. 11D), integration to the adjacent cartilage (FIG. 11E), smooth surface with minimal fibrillation.

Example 8: Fibrocartilage Formation in the Donor Site in the ICA

FIGS. 12A-12D show the arthroscopic evaluation of the osteochondral biopsy taken at the autologous chondrocyte implantation (FIGS. 12A and B). Subsequently, a second arthroscopic view 12 months after the autologous chondrocyte implantation clearly shows filling of the donor area with abundant presence of fibrous, irregular and fibrillar tissue (FIGS. 12C and D); a process that is avoided in the implantation of cadaveric chondrocytes.

Example 9: Follow-Up of Some Patients Treated with the Graft of the Present Invention In the following, the data of 4 patients treated with the graft or construct of the present invention and the evaluation of different lesions, parameters and evolution times are presented in summary form.

TABLE 2

Demographic report of patients implanted with the present invention.

| Patient | Genre | Age | Joint | Evolution Months | Lesion Size (mm) | BMI |
|---|---|---|---|---|---|---|
| 1 | Male | 43 | Hip | 9 | 40 | 26 |
| 2 | Female | 39 | Knee | 7 | 60 | 25 |
| 3 | Female | 16 | Knee | 3 | 60 | 25 |
| 4 | Male | 15 | Ankle | 3 | 25 | 22 |

From the information contained in the table it is clear that patients of various ages were treated, from young (15 years) to adult patients (43 years) with lesions in different joints such as ankle, knee and hip; with lesions with an average size of 37 mm (25-60 mm). FIGS. 13A-13D and 15A-15F show the intervention with the implant or construct of the present invention for hip and knee, respectively.

During the follow-up of these patients, the intensity and frequency of pain before and after treatment were evaluated. Pain intensity was evaluated with the Visual Analog Scale (VAS), which allows measuring the intensity of pain described by the patient with the maximum reproducibility, which consists of 10 points; the higher the numerical value, the greater the pain intensity. The frequency of pain was also identified in 5 categories: never, rarely, sometimes, often or always. This measurement was taken before surgery and 3 months after surgery. In the first two patients the pain decreased considerably from a maximum of 9 points to a value of 2 points.

TABLE 3

Assessment of pain intensity and frequency, before and after treatment.

| Patient | VAS pre-op | Frequency | VAS 3 m | Frequency | Pain reduction value |
|---|---|---|---|---|---|
| 1 | 7 | Always | 1 | Rarely | 6 points |
| 2 | 9 | Always | 2 | Rarely | 7 points |

VAS = Visual Analog Score.

The results of the table show that only 3 months after the intervention, with the graft of the present invention, there is a significant decrease in both the intensity and frequency of pain in adult patients with hip and knee intervention, respectively. Pain decreased on average 6.5 points (before versus at 3 and 6 months follow up) from a maximum value of 9.

Likewise, in the follow-up of these patients, the arches of mobility before and after treatment were also evaluated, using conventional techniques, avoiding the mobility associated with the lumbar spine, in the supine and prone or lateral decubitus positions.

TABLE 4

Improvement of hip mobility arches after 3 and 6 months after implantation.

| Evaluation | Flexion | Extension | Abduction | Adduction | IR | ER |
|---|---|---|---|---|---|---|
| Healthy hip | 120 | 20 | 50 | 40 | 35 | 20 |
| Operated hip (pre-op) | 60 | 0 | 15 | 20 | 15 | 0 |
| Operated hip (3 m) | 75 | 5 | 20 | 25 | 25 | 10 |
| Operated hip (6 m) | 90 | 10 | 30 | 30 | 30 | 10 |
| Improvement (degrees) | 30 | 10 | 15 | 10 | 15 | 10 |

IR = Internal Rotation;
ER = External Rotation.

Comparison of the ranges of mobility of the operated hip versus the healthy hip before surgery, at 3 and 6 months after the implant was placed, in which a significant improvement is observed in all mobility arches. The results show a clear improvement in all values for the different types of hip movement.

Additionally, the success of a treatment is also determined through the patients' joint function, evaluated by means of internationally validated clinical scales, where parameters such as pain level, inability to perform activities of daily living, sports activities and quality of life are reported. The scales are different for hip and knee and provide a numerical score that was evaluated before and after surgery.

FIGS. 17A-17B show the evaluation of hip joint function before and after (6 months) the intervention with the implant of the present invention.

In the same way, the arches of mobility before and after the knee treatment were evaluated:

TABLE 5

Improvement of the arches of mobility in the knee after 3 months of the implant.

| Evaluation | Flexion | Extension | Valgus |
|---|---|---|---|
| Healthy knee | 135 | 0 | 7 |
| Operated knee (pre-op) | 120 | 0 | 7 |
| Operated knee (3 m) | 130 | 0 | 7 |
| Improvement | 10 | 0 | NA |

Comparison of the ranges of mobility of the operated knee versus the healthy knee before surgery and 3 months after the implant of the present invention has been placed, in which a significant improvement in flexion is observed, only a deficit of only 5° (130°) with respect to the healthy knee (135°) is observed at 3 months of follow-up.

Similarly, FIGS. 18A-18D show the evaluation of knee joint function before and after the operation (3 months), in all of which the improvement in various functional parameters can be clearly seen.

In addition, these patients were evaluated for the quality of repair tissue vs. healthy cartilage at 3 months, the results of which are shown in Table 6 below. One of the main non-invasive methods for assessing the quality of repair tissue in the treatment of cartilage lesions is T2-mapping. This is one of the worldwide recognized techniques for the study of cartilage. It maps the values of physical parameters which show the water relaxation time observed in the structure of interest. This value is established for cartilage, ranging from 20 to 50 milliseconds in normal cartilage; values within the normal range indicate that the repair tissue has a quality very similar to that of native cartilage (hyaline cartilage) and its durability is better, on the contrary, values outside this range indicate that the tissue is of poor quality (very fibrous or with a tendency to form bone), with a high susceptibility to deteriorate over time.

TABLE 6

Values of repaired cartilage vs. native cartilage.

| Patient | Joint | Zone | ROI-1 (healthy) | ROI-2 (operated) | Difference (ms) |
|---|---|---|---|---|---|
| 1 | Hip | Anterior | 48.2 | 55.5 | 7.3 |
| 1 | Hip | Posterior | 47.5 | 50.5 | 3 |
| 2 | Knee | Lateral-central | 47.7 | 56.9 | 9.2 |

FIG. 14A-14B show the corresponding T2 mapping for the hip, while FIG. 16 shows the corresponding T2 mapping for the knee. The values of the water relaxation time, at 3 months post-operation in the first two patients, were found to be elevated with respect to the normal values of healthy cartilage (ROI-1 vs ROI-2), which is an expected behavior, the same behavior has been observed in the already reported techniques of Autologous Chondrocyte Implantation, since the repair tissue begins to mature and transform into cartilage around 12 months. It is expected that in subsequent evaluations (6 and 12 months) these values will decrease and approach healthy cartilage values.

While some preferred embodiments of the present invention have been shown and described herein, it will be obvious to those skilled in the art that such embodiments are provided for illustrative purposes only. Numerous variations, changes and substitutions will occur to those skilled in the art without departing from the spirit of the invention and should therefore be considered within the scope of protection of the present invention. It should be understood that various alternatives to the embodiments of the invention described herein may be employed in the practice of the invention. It is intended that the following claims define the scope of the invention and that methods and structures within the scope of these claims and their equivalents are thereby covered.

REFERENCES

1. Olivos-Meza A, Cortés-González S, Ferniza-Garza J J, Pérez-Jiménez F J, Villalobos-Córdova, Ibarra J C. Arthroscopic Treatment of Patellar and Trochlear Cartilage Lesions with Matrix Encapsulated Chondrocyte Implantation versus Microfracture: Quantitative Assessment with MRI T2-Mapping and MOCART at 4-Year Follow-up. Cartilage 2019:1-3.
2. Arredondo R, Olivos-Meza A, Villalobos E, Cortés S, Pérez-Jiménez F J, et. al. Una nueva técnica artroscópica de implante de condrocitos autólogos en matriz encapsulada (ICAME) en patela: evaluación clinica y por mapeo T2 a 4 años de seguimiento. Revista Española de Artroscopia y Cirugía Articular 2018; 25(61):30-41.

3. Orth P, Gao L, Madry H. Microfracture for cartilage repair in the knee: a systematic review of the contemporary literature. Knee Surgery, Sports Traumatology, Arthroscopy 2019:1-8.

4. Holt K, Sorhaindo M, Coady C, Ho-Bun Wong I. Arthroscopic Treatment of Medial Femoral Knee Osteochondral Defect Using Subchondroplasty and Chitosan-Based Scaffold. Arthrosc Tech. 2019 April; 8(4): e413-e418.

5. Martín AR, Patel J M, Zlotnick H M, Carey J L, Mauck R L. Emerging therapies for cartilage regeneration in currently excluded 'red knee' populations. Regenerative Medicine 2019; 12:1-10.

6. Mistry H, Connock M, Pink J, Shyangdan D, Clar C, Royle P, et al. Autologous chondrocyte implantation in the knee: systematic review and economic evaluation. Health Technol Assess 2017; 21(6).

7. Taylor A, Lee P. Single Treatment Autologous Chondrocyte Implantation: The Next Generation of ACI. Can J Biomed Res & Tech 2019; 2(2): 1-4.

8. Davies R L, Kuiper N. Regenerative Medicine: A Review of the Evolution of Autologous Chondrocyte Implantation (ACI) Therapy. Bioengineering 2019; 6(22): 2-16.

9. Olivos-Meza A, Velasquillo-Martínez C, Olivos-Díaz B, Landa-Solís C, Brittberg M, et. al. Co-culture of dedifferentiated and primary human chondrocytes obtained from cadaveric donor enhance the histological quality of repair tissue: an in-vivo animal study. Cell Tissue Bank 2017; 14(3):1-12.

The invention claimed is:

1. An implant or construct for the treatment of cartilage lesions in joints of a human subject comprising:

a) a population of cadaveric P0 chondrocytes isolated from a cartilage of a cadaveric young human donor having an age range of 14 to 20 years, b) the chondrocytes are seeded onto a hyaluronic acid scaffold, c) the seeded chondrocytes are sealed with a fibrin glue, wherein the sealed chondrocytes are cultured in a culture medium containing an autologous serum for a period of 5 to 7 days prior to use;

d) wherein the cadaveric P0 chondrocytes have been cryopreserved; and e) wherein the chondrocytes of the implant induce the formation of a hyaline cartilage having a modified O'Driscoll histological score of 9.57±1.27 (mean SD), with the formation of isogenic groups and an extracellular matrix displaying markers characteristic of a hyaline cartilage.

2. The implant or construct for the treatment of cartilage lesions in joints of a human subject according to claim 1, wherein the chondrocytes P0 chondrocytes are seeded at a density of $1 \times 10^6$ cells/cm$^2$ and are cultured at 37° C., 5% $CO_2$ and 5% humidity, with DMEM-F12 culture medium containing 10% of autologous serum and 1% of antibiotic-antimycotic.

3. The implant or construct for the treatment of cartilage lesions in joints of a human subject in accordance with claim 2, wherein the implant chondrocytes induce the formation of extracellular matrix with characteristic markers of hyaline cartilage.

* * * * *